US009562257B2

(12) United States Patent
Keiler et al.

(10) Patent No.: US 9,562,257 B2
(45) Date of Patent: Feb. 7, 2017

(54) ANTIBACTERIAL AND PLASMID ELIMINATION AGENTS

(71) Applicant: THE PENN STATE RESEARCH FOUNDATION, University Park, PA (US)

(72) Inventors: Kenneth C Keiler, Boalsburg, PA (US); Stephen J Benkovic, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 14/136,261

(22) Filed: Dec. 20, 2013

(65) Prior Publication Data

US 2014/0187443 A1    Jul. 3, 2014

Related U.S. Application Data

(63) Continuation of application No. 12/111,096, filed on Apr. 28, 2008, now Pat. No. 8,637,267, which is a continuation-in-part of application No. 11/758,995, filed on Jun. 6, 2007, now abandoned.

(60) Provisional application No. 60/914,129, filed on Apr. 26, 2007, provisional application No. 60/811,967, filed on Jun. 7, 2006.

(51) Int. Cl.
| | |
|---|---|
| *C07H 21/04* | (2006.01) |
| *C12N 15/67* | (2006.01) |
| *C12Q 1/66* | (2006.01) |
| *C12N 15/10* | (2006.01) |
| *C12Q 1/68* | (2006.01) |

(52) U.S. Cl.
CPC ............. *C12Q 1/66* (2013.01); *C12N 15/1086* (2013.01); *C12N 15/67* (2013.01); *C12Q 1/6897* (2013.01)

(58) Field of Classification Search
None
See application file for complete search history.

(56) References Cited

U.S. PATENT DOCUMENTS

2006/0078875 A1    4/2006   Benkovic

OTHER PUBLICATIONS

DeWet et al., Mol. Cell. Biol., 7(2):725-737, 1987.*
Horswill, et al.; A Systematic Method for Identifying Small-Molecule Modulators of Protein Interactions; PNAS, vol. 101, No. 44, 2004, pp. 15591-15596.
Khlebnikov, et al.; Homogeneous Expression of the Pbad promoter in *Escherichia coli* by Constitutive Expression of the Low-Affinity High-Capacity AraE Transporter; Microbiology, 2001, vol. 147; pp. 3241-3247.
Scott, et al.; "Production of Cyclic Peptides and Proteins in vivo"; PNAS, 1999; vol. 96, No. 24; pp. 13638-13643.
Horswill and Benkovic; "Cyclic Peptides, a Chemical Genetics Tool for Biologists"; Cell Cycle, 2005, vol. 4, Issue 4; pp. 552-555.
Datsenko and Wanner; "One-Step Inactivation of Chromosomal Genes in *Escherichia coli* K-12 Using PCR Products"; PNAS; 2000, vol. 97, No. 12; pp. 6640-6645.
Lessner, et al.; "Proteolytic Adaptor for Transfer-Messenger RNA-Tagged Proteins From Alpha-Proteobacteria"; Journal of Bacteriology, Jan. 2007; vol. 189, No. 1; pp. 272-275.
Abel-Santos, et al.; "Use of Inteins for the In Vivo Production of Stable Cyclic peptide Libraries in *E. coli*"; Methods in Molecular Biology; vol. 205; 2003; pp. 281-294.
Livermore; "Multiresistence and 'Superbugs'"; Communicable Disease and Public Health; vol. 1, No. 2, 1998; pp. 74-76.
Wah, et al.; "Flexible Linkers Leash the Substrate Binding Domain of SspB to a Peptide Module that Stabilizes Delivery Complexes with the AAA+ ClpXP Protease"; Molecular Cell, vol. 12, 2003; pp. 355-363.
Scott, et al.; "Structural Requirements for the Biosynthesis of Backbone Cyclic Peptide Libraries"; Chemistry & Biology 8 (2001); pp. 801-815.
Park, et al.; "Structural Basis of SspB-tail Recognition by the Zinc Binding Domain of ClpX"; J. Mol. Biol. (2007) 367; pp. 514-526.
Levchenko, et al.; "A Specificity-Enhancing Factor for the ClpXP Degradation Machine"; Science, 2000, vol. 289; pp. 2354-2356.

* cited by examiner

*Primary Examiner* — Nancy Treptow
(74) *Attorney, Agent, or Firm* — Husch Blackwell LLP

(57) ABSTRACT

Inhibitors of the tmRNA pathway have antibacterial activity with broad species specificity, including *B. anthracis* and other pathogens of military and civilian interest. Identified cyclic or linear peptides are further selected by in vivo selection methods, kill bacterial pathogens when added exogenously, and/or eliminate plasmids carrying antibiotic resistance or virulence genes. The molecular target of each cyclic peptide is in the tmRNA pathway and the tmRNA pathway is inhibited in vitro and in vivo by the addition of the peptides.

12 Claims, 11 Drawing Sheets

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial sequence
<220> FEATURE:
<223> OTHER INFORMATION: synthetic sequence

<400> SEQUENCE: 1

Ser Gly Trp Arg Val Gln Gly Pro Leu
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic sequence

<400> SEQUENCE: 2

Ser Gly Ser Lys Gly Val Leu Pro Leu
1               5

<210> SEQ ID NO 3
<211> LENGTH: 12
<212> TYPE: PRT
<213> ORGANISM: Artificial sequence
<220> FEATURE:
<223> OTHER INFORMATION: Synthetic sequence

<400> SEQUENCE: 3

Cys Arg Gly Gly Arg Pro Ala Leu Arg Val Val Lys
1               5                   10
```

<210> SEQ ID NO 4
<211> LENGTH: 8
<212> TYPE: PRT
<213> ORGANISM: Artificial sequence
<220> FEATURE:
<223> OTHER INFORMATION: Synthetic sequence

<400> SEQUENCE: 4

Ser Gly Trp Pro Tyr Lys Trp Met
1               5

<210> SEQ ID NO 5
<211> LENGTH: 8
<212> TYPE: PRT
<213> ORGANISM: Artificial sequence
<220> FEATURE:
<223> OTHER INFORMATION: Synthetic sequence

<400> SEQUENCE: 5

Ser Gly Trp His Arg Arg Gly Met
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic sequence

<400> SEQUENCE: 6

Ser Gly Trp Tyr Gly Arg Arg His
1               5

<210> SEQ ID NO 7
<211> LENGTH: 11
<212> TYPE: PRT
<213> ORGANISM: Artificial sequence
<220> FEATURE:
<223> OTHER INFORMATION: Synthetic sequence

<400> SEQUENCE: 7

Ala Ala Asn Asp Glu Asn Tyr Ala Leu Ala Ala
1               5                   10

<210> SEQ ID NO 8
<211> LENGTH: 11
<212> TYPE: PRT
<213> ORGANISM: Artificial sequence
<220> FEATURE:
<223> OTHER INFORMATION: Synthetic sequence

<400> SEQUENCE: 8

Ala Ala Asn Asp Glu Asn Tyr Ala Leu Asp Asp
1               5                   10

<210> SEQ ID NO 9
<211> LENGTH: 70
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature

```
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 9
ggaattcgcc aatggggcga tcgcccacaa ttccggctgg nnsnnsnnsn nsnnstgctt    60
aagttttggc                                                           70

<210> SEQ ID NO 10
<211> LENGTH: 33
<212> TYPE: DNA
<213> ORGANISM: Artificial sequence
<220> FEATURE:
<223> OTHER INFORMATION: Synthetic sequence

<400> SEQUENCE: 10
ggaattcaag ctttcattga agctgccaca agg                                  33

<210> SEQ ID NO 11
<211> LENGTH: 25
<212> TYPE: DNA
<213> ORGANISM: Artificial sequence
<220> FEATURE:
<223> OTHER INFORMATION: Synthetic sequence

<400> SEQUENCE: 11
ggaattcgcc aatggggcga tcgcc                                           25

<210> SEQ ID NO 12
<211> LENGTH: 8
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (4)..(8)
<223> OTHER INFORMATION: X is any amino acid

<400> SEQUENCE: 12

Ser Gly Trp Xaa Xaa Xaa Xaa Xaa
1               5

<210> SEQ ID NO 13
<211> LENGTH: 9
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(7)
<223> OTHER INFORMATION: X is any amino acid

<400> SEQUENCE: 13

Ser Gly Xaa Xaa Xaa Xaa Xaa Pro Leu
1               5
```

```
<210> SEQ ID NO 14
<211> LENGTH: 9
<212> TYPE: PRT
<213> ORGANISM: Artificial sequence
<220> FEATURE:
<223> OTHER INFORMATION: Synthetic sequence

<400> SEQUENCE: 14

Ser Gly Gly Arg Gly Gly Arg Pro Leu
1               5

<210> SEQ ID NO 15
<211> LENGTH: 11
<212> TYPE: PRT
<213> ORGANISM: Artificial sequence
<220> FEATURE:
<223> OTHER INFORMATION: Synthetic sequence

<400> SEQUENCE: 15

Arg Gly Gly Arg Pro Ala Leu Arg Val Val Lys
1               5                   10
```

ANTIBACTERIAL AND PLASMID ELIMINATION AGENTS

CROSS-REFERENCE TO RELATED APPLICATION

The present application is a continuation of U.S. patent application Ser. No. 12/111,096, now U.S. Pat. No. 8,637,267, filed Apr. 28, 2008, which is a continuation-in-part of U.S. patent application Ser. No. 11/758,995, filed Jun. 6, 2007, now abandoned, which claims the priority of U.S. provisional patent application No. 60/811,967 filed Jun. 7, 2006 and U.S. provisional patent application No. 60/914,129 filed Apr. 26, 2007, which are incorporated herein by reference.

STATEMENT AS TO FEDERALLY SPONSORED RESEARCH

The invention was made with government support under Grant No. GM068720 awarded by the National Institutes of Health under Contract No. W911NF-06-1-0144, awarded by the U.S. Army/ARO. The Government has certain rights in the invention.

FIELD OF THE INVENTION

The invention relates to inhibitors of the tmRNA pathway from libraries of cyclic and linear peptides.

BACKGROUND

Dispersal of weaponizable bacterial pathogens among foreign states and terrorists poses a significant military and public health threat. For example, *Bacillus anthracis* was used by a terrorist in the United States, Saddam Hussein's Iraq was known to have had bioweapons programs involving anthrax and brucellosis, and Russia has an extensive biowarfare program involving a wide array of natural and engineered bacteria. Conventional classes of antibiotics are generally effective against pathogens such as *Bacillus anthracis*, but several challenges demand that new classes of broad-spectrum antibiotics be developed for troop preparedness and biodefense. First, the natural spread of antibiotic resistance genes in bacterial populations has lead to decreasing options for antibiotic therapy. Many natural isolates of *B. anthracis* are now resistant to penicillin, and for other pathogens, such as *Brucella* species and *Mycobacterium tuberculosis*, treatment is often limited to drugs with serious risks or side effects. Second, the intentional engineering of resistance to known classes of antibiotics into biowarfare agents could significantly increase the severity and duration of infection due to biological attacks. Third, relatively benign pathogens can be engineered to kill infected patients upon treatment with conventional antibiotics. For example, pertussis toxin could be cloned under the control of a tetracycline-inducible promoter in *Chlamydia* so that the standard antibiotic treatment leads to rapid death. Fourth, unknown species or species for which there is not a rapid diagnostic test may be developed as biowarfare agents, requiring treatment before a diagnosis has been made. Novel broad-spectrum antibiotics could be used to treat unknown pathogens and pathogens resistant to known classes of antibiotics.

There is thus a need in the art to provide novel agents which have antibacterial activity to which bacteria do not develop resistance.

SUMMARY

The invention describes novel broad-spectrum antibiotics and methods of production thereof. Novel antibiotics that directly kill bacteria are developed by identifying inhibitors of essential pathways not targeted by other classes of antibiotics. These inhibitors can be broad-spectrum antibiotics if the pathway that is inhibited is essential for pathogenesis in many organisms of interest. The tmRNA pathway for translational regulation is an appropriate target for novel antibiotics because it is not targeted by other drugs, it is present in all bacteria, and it is essential for virulence in several pathogens. Targeting a known pathway such as tmRNA allows rapid characterization of the method of action of the identified antibiotics. Identifying the method of action is essential for late stage drug development and for regulatory approval, and is frequently a significant challenge for drugs with an unknown molecular target. Another strategy for antibiotic development is to identify agents that eliminate plasmids carrying virulence or antibiotic resistance genes. Plasmid elimination agents can also be used to eliminate plasmid-borne antibiotic resistance genes, so that the efficacy of available classes of antibiotics can be increased. For example, *Staphylococcus aureus* can carry plasmids encoding resistance to many antibiotics, rendering them very difficult to treat. Elimination of the plasmids would allow effective treatment with drugs such as chloramphenicol. The tmRNA pathway is required for plasmid maintenance in some species of bacteria, so inhibitors of this pathway are likely to be efficient plasmid elimination agents.

In a preferred embodiment, a method of identifying bactericidal peptides comprises attaching a fluorescent protein to a tmRNA encoded peptide to produce a reporter for proteolysis of tmRNA-tagged proteins; identifying tmRNA pathways to which cyclic peptides can be targeted to inhibit tmRNA-tagged protein degradation; identifying cyclic peptides which inhibit tmRNA-tagged protein degradation at different steps of said pathways; administering cyclic peptides which inhibit degradation of tmRNA-tagged proteins, to a bacterial cell; and, identifying cyclic peptides with bactericidal activity. Preferably, the reporter comprises a tmRNA tag sequence at a 3' end of a gene encoding a fluorescent protein.

In a preferred embodiment, the peptides are cyclic peptides, and/or linear peptides.

In another preferred embodiment, the fluorescent protein comprises green fluorescent protein (GFP), red fluorescent protein (RFP), blue fluorescent protein (BFP) or yellow fluorescent protein (YFP). Preferably, the fluorescent protein is green fluorescent protein (GFP) and yellow fluorescent protein (YFP). We have found that mCherry and variants thereof are also excellent reporters.

In another preferred embodiment, degradation of the tmRNA-tagged protein is monitored by loss of fluorescence.

In another preferred embodiment, a bacterial cell comprises a fluorescent protein expressing gene-tagged tmRNA reporter construct is transformed with cyclic peptide expressing plasmid library.

In another preferred embodiment, the cyclic peptide expressing plasmid library expresses peptides of at least about five amino acids up to twenty amino acids. Preferably, the cyclic peptide expressing plasmid library is generated by randomly substituting at least 50% of nucleic acids coding for the cyclic peptides with an NNS sequence, wherein N=A, G, T, or C and S=G or C.

In a preferred embodiment, the peptides are cyclic peptides, and/or linear peptides.

In one preferred embodiment, the cyclic peptide comprises any one or more of SEQ ID NO's: 1-9.

In another preferred embodiment, a composition comprises attaching a fluorescent protein to a tmRNA encoded peptide to produce a reporter for proteolysis of tmRNA-tagged proteins. Preferably, the reporter comprises a tmRNA tag sequence at a 3' end of a gene encoding a fluorescent protein. Preferably, the fluorescent protein expressing gene is selected from the group consisting of green fluorescent protein (GFP), red fluorescent protein (RFP), blue fluorescent protein (BFP) or yellow fluorescent protein (YFP). mCherry and variants too.

In one preferred embodiment, the fluorescent protein expressing gene is egfp.

In another preferred embodiment, an isolated cell comprises a tmRNA tag at the 3' end of a fluorescent protein expressing gene and cyclic peptide expressing plasmid library express peptides of at least about five amino acids up to twenty amino acids. Preferably, the cyclic peptide expressing plasmid library is generated by randomly substituting at least 50% of nucleic acids coding for the cyclic peptides with an NNS sequence, wherein N=A, G, T, or C and S=G or C. Preferably, the peptides are cyclic peptides, and/or linear peptides.

In another preferred embodiment, the cyclic peptide comprises any one or more of SEQ ID NO's: 1-9.

In another preferred embodiment, the cyclic peptide expressing plasmid library is under control of an inducible promoter.

In another preferred embodiment, a method of identifying tmRNA pathway inhibitors comprises transforming a cell culture with a tmRNA tagged fluorescent protein expressing vector; transforming said cell culture with a cyclic peptide library; inducing expression of said cyclic peptide library with an inducing agent; measuring fluorescence of said cells; and, identifying tmRNA pathway inhibitors. Preferably, fluorescence is measured by FACS analysis. Cells comprising a cyclic peptide and have a high fluorescence are isolated and the cyclic peptide is purified and tested for bactericidal activity, and molecular targets are identified. Preferably, the peptides are cyclic peptides, and/or linear peptides.

In another preferred embodiment, a method of identifying cyclic peptides which eliminate plasmids from a cell, comprises incubating a bacterial cell culture with a purified cyclic peptide; culturing said bacterial cell cultures on selective medium; determining colony forming units as compared to control; wherein, decreased colony forming units as compared to a control are indicative of plasmid elimination; and, cyclic peptides which eliminate plasmids from a cell. Preferably, the peptides are cyclic peptides, and/or linear peptides.

In another preferred embodiment, a method of identifying cyclic peptide molecular targets, comprises combining tmRNA, a molecular target and cyclic peptide; measuring inhibition of tagging activity of tmRNA in the presence of the purified cyclic peptide as compared to a non-inhibiting cyclic peptide control; and, identifying a cyclic peptide molecular target. Preferably, tagging is measured by incorporation of into a radioactive label in a molecular target, such as for example, $^{14}$C-alanine In another preferred embodiment, the inhibition of tmRNA tagging is further identified using reporter strains expressing fluorescent labels. For example, the reaction that is targeted by each inhibitor is identified using EYFP-trpAt and EGFP-tag reporter strains Inhibitors of tmRNA tagging produce yellow fluorescence when incubated with the EYFP-trpAt strain, but no fluorescence when incubated with the EGFP-tag strain and inhibitors of proteolysis of tagged proteins produce fluorescence when incubated with either strain.

In another preferred embodiment, a method of treating a bacterial disease or complications thereof, comprises administering one or more cyclic peptide compounds which target tmRNA pathways. Complications, include, but not limited to septicemia.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 4A is a schematic diagram of SICLOPPS library construction. Three fixed and five randomized codons were cloned in the coding region between the intein IC and IN domains When this gene is expressed, the IC and IN domains promote circular ligation of the intervening peptide, resulting in 8-mer cyclic peptides with 5 random amino acids. FIG. 4B is a schematic diagram showing the GFP-tag reporter. The tmRNA peptide tag sequence was encoded at the 3' end of the gfp gene under control of an IPTG-inducible promoter. All GFP produced from this gene will have the tmRNA peptide tag at the C terminus. FIG. 4C shows the result of expression of the GFP-tag reporter and inhibitory cyclic peptides in E. coli. Production of GFP-tag was induced in wildtype E. coli (wt), a strain lacking the clpX gene (ΔclpX), and a strain that was also producing the IXP1 cyclic peptide, and the cells were imaged by immunofluorescence (fluor.) to see fluorescent cells and differential interference contrast microscopy (DIC) to see all cells. In wild type, SspB binds to the tmRNA peptide at the C terminus of GFP-tag and tethers the protein to the ClpXP protease, resulting in rapid degradation and no fluorescent cells. In the ΔclpX strain, the absence of active ClpXP protease results in stabilization of GFP-tag and highly fluorescent cells. In wild-type cells producing IXP1, the cyclic peptide inhibits degradation of GFP-tag, resulting in fluorescent cells. DIC images show that the ΔclpX cells and wild-type cells producing IXP1 are also slightly filamentous.

FIG. 6A is a chromatogram showing IXP1 incubated with ClpXP for 60 min and samples before (0 min) and after (60 min) incubation were analyzed by reverse-phase HPLC. Plots of the absorbance at 280 nm versus time after injection are shown with arrows indicating the retention time for cyclic IXP1 and linear IXP1 as determined from control assays without ClpXP. The area under the cyclic peptide peaks was unchanged after 60 min. FIG. 6B is a graph showing the effects of IXP1 on the ATPase activity of ClpX with and without GFP-tag, and on the peptidase activity of ClpP, were measured. Each assay was normalized to the activity in the absence of IXP1. Error bars indicate the standard deviation at each IXP1 concentration.

FIG. 8A—tmRNA tag codons are cloned at the 3' end of a reporter gene such as gfp, resulting in a protein that is degraded unless an inhibitor of ClpXP is present. FIG. 8B—a sequence that targets the reporter to the tmRNA pathway is cloned in the gene such that the reporter is tagged and degraded unless a tmRNA inhibitor is present. FIG. 8C—compatible reporters for tmRNA and ClpXP can be used in tandem to simultaneously identify inhibitors of each step of the pathway.

DETAILED DESCRIPTION

The development and identification of lead compounds from a library of cyclic peptides that are potent inhibitors of the tmRNA pathway, a novel target that is essential for viability or pathogenesis in a wide variety of bacteria is provided. In particular, screening methods for identification of tmRNA pathway inhibitors; identification and optimize inhibitors from libraries of cyclic peptides; testing the bactericidal and plasmid elimination efficacy of lead compounds against *B. anthracis* and other pathogens are provided.

Cyclic Peptides and tmRNA

Figure 1A:
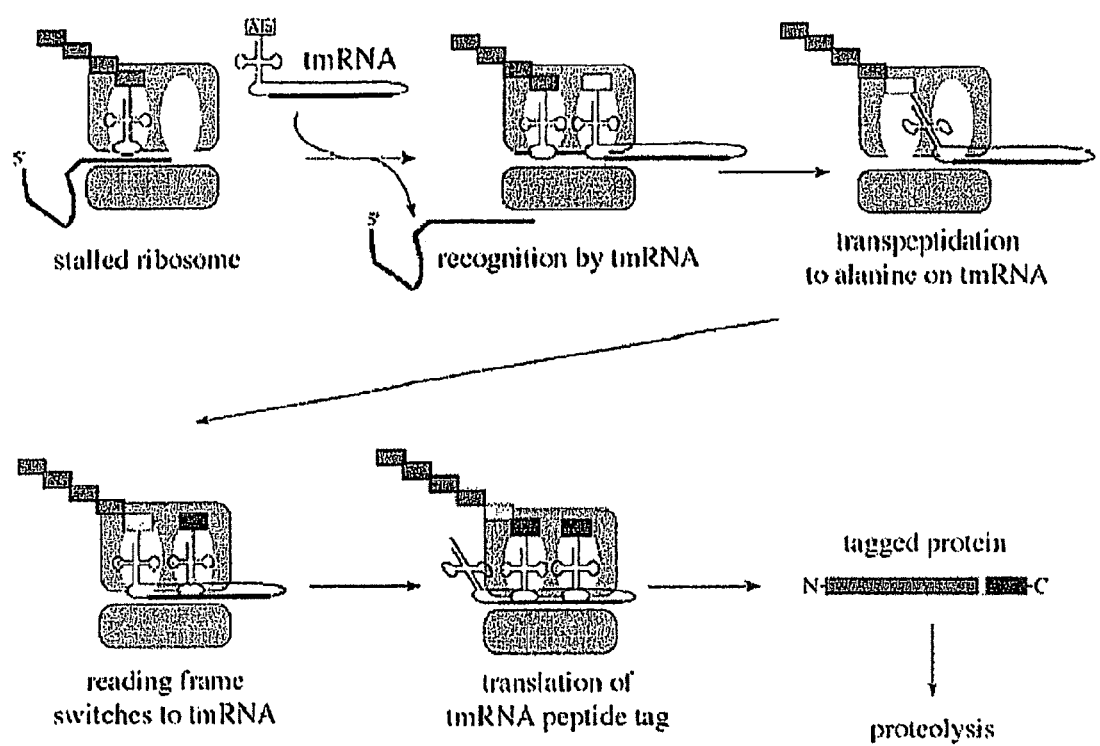
FIG. 1A is a schematic diagram showing the tmRNA pathway.

The discovery of small molecule inhibitors of specific enzymes is a common practice in the discovery of antibiotics and pharmacological reagents. However, many approaches, such as rational design, require detailed knowledge of the enzyme's structure or mechanism. In addition, inhibitors that are developed in vitro may not be effective in vivo. The goal of these studies was to establish methods for rapidly screening a pool of possible inhibitors that will be effective in bacteria Inhibitors were sought from a library of cyclic peptides produced in bacteria using Split Intein Circular Ligation of Proteins and Peptides (SICLOPPS) technology. SICLOPPS uses the chemistry of inteins, naturally occurring protein-splicing sequences, to ligate the amino and carboxy termini of an encoded peptide to produce a cyclic polypeptide. Cyclic polypeptides from 5 to more than 150 residues have been produced using SICLOPPS. Because the splicing reaction is spontaneous in bacteria, SICLOPPS can be used to generate libraries of cyclic peptides that are amenable to genetic manipulation by randomizing the DNA sequence that encodes the polypeptide that will be cyclized. Such libraries have been used to search for inhibitors of protein-protein interactions. Cyclic peptides are good candidates for inhibitor screening because they have a large sequence diversity, they are more stable than linear peptides in vivo, and several natural antibiotics are cyclic peptides. See, for example, published U.S. application No: US 2006/0078875 and Abel-Santos et al. (2003) Methods Mol. Biol. 205:281-294 incorporated by reference in its entirety herein.

The tmRNA protein tagging and degradation pathway was chosen as a target for inhibitor selection because this pathway is found in all bacteria, and is essential for virulence in several pathogenic strains. tmRNA is an active RNA molecule that enters translational complexes to add a peptide tag to the C terminus of proteins before they are released from the ribosome. The tmRNA-encoded peptide contains epitopes for several intracellular proteases and most tagged proteins are rapidly degraded. In *E. coli*, most of the cytoplasmic proteins tagged by tmRNA are recognized by a proteolytic specificity factor, SspB, which facilitates degradation by the ClpXP protease. ClpXP is a multisubunit protease that degrades a variety of substrates in addition to tmRNA-tagged proteins. Components of the tmRNA pathway are highly conserved in bacteria: tmRNA has been found in all bacterial genomes, and ClpXP is conserved in all groups except mycoplasmas. Moreover, components of this pathway are essential in species of *Neisseria* and *Shigella*, and required for virulence in species of *Salmonella* and *Vibrio*, so inhibitors of this pathway are good lead compounds for antibiotic development. Cyclic peptides that inhibited the degradation of tmRNA-tagged proteins by ClpXP were selected from a library produced using SICLOPPS. These inhibitors acted at different steps in the ClpXP mechanism, and affected the degradation of other ClpXP substrates in different ways, indicating that cyclic peptides could be selected with different properties. These cyclic peptides were bactericidal against bacteria that require ClpXP activity.

The tmRNA pathway: The tmRNA pathway is an excellent target for the identification of novel antibiotics for several reasons: 1) tmRNA is essential for viability, virulence, or plasmid maintenance, so inhibitors should directly kill bacteria, and cure plasmids from bacteria to eliminate virulence or drug resistance; 2) tmRNA is not targeted by any current drugs, so antibiotics that attack this pathway are novel; and 3) and tmRNA is found in all bacteria but no animals, so inhibitors of this pathway should be effective against a wide array of pathogens but have little interaction with the human host. In preferred embodiments, the tmRNA pathway is targeted for potential drug targets.

tmRNA is a small, noncoding RNA that regulates protein translation and gene expression in bacteria. This highly structured RNA is found in all bacterial species and is one of the most abundant RNAs in the cell, found at 5-10% the level of rRNA. The name tmRNA is derived from the ability of this molecule to act as both a tRNA and an mRNA. The 5' and 3' ends of tmRNA fold into a structure resembling a tRNA, and the 3' end is charged with alanine by alanyl-tRNA synthetase. Using this tRNA-like structure, tmRNA can invade a ribosome during translation, with the mRNA and nascent polypeptide still engaged (FIG. 1A). tmRNA enters the ribosomal A site and forces the ribosome to expel the mRNA and rearrange its decoding center on a specialized open reading frame within tmRNA. Translation of the tmRNA reading frame results in the addition of a short peptide to the C terminus of the nascent polypeptide. The tmRNA-encoded peptide tag contains epitopes for several proteases, and results in rapid proteolysis of the tagged protein. The net effect of tmRNA activity on a translational complex is degradation of the engaged protein and mRNA, and release of the ribosome. Several events have been shown to target translation complexes to the tmRNA pathway, including damage to the mRNA, blocks in translation that result in an incomplete mRNA, and lack of cognate tRNA or release factor for translation elongation or termination. In many of these cases the function of tmRNA activity may be to remove incomplete proteins and release ribosomes that cannot continue translation of the engaged mRNA. In other cases, tmRNA is important for regulation of gene expression, although the mechanism for targeting translation complexes to the tmRNA pathway in these cases has not been elucidated.

tmRNA is clearly a critical component of bacteria. Not only is it very abundant and universally conserved, but mutations in tmRNA have severe phenotypes. tmRNA is essential for viability in pathogenic species of *Neisseria*, *Shigella*, and enteroinvasive *E. coli* (EIEC). tmRNA activity is also required for virulence of *Salmonella typhimurium*, plant cell invasion by *Bradyrhizobium japonicum*, and normal growth of *Caulobacter crescentus*, a model bacterium which is closely related to *Brucella* and *Rickettsia* species. Interestingly, although the tmRNA pathway is essential in pathogenic *E. coli*, mutations in tmRNA cause only a slow growth phenotype in cultured laboratory strains of *E. coli* such as K12. Presumably the severe mutagenesis required to domesticate wild-type *E. coli* isolates introduced mutations that partially bypass the requirement for tmRNA. This project will take advantage of this phenotype by selecting for inhibitors of the tmRNA pathway in *E. coli* K12. Because tmRNA pathway inhibitors will not kill *E. coli* K 12, inhibitors can be identified and characterized in vivo using genetic screening techniques. When selected inhibitors are introduced to pathogenic bacteria, where the tmRNA pathway is essential for virulence, they are expected to result in cell death or plasmid elimination. The principle assumption behind this strategy is that compounds that inhibit the tmRNA pathway in *E. coli* K12 will kill bacteria in which the pathway is essential. Experiments are described in detail in the examples which follow.

There are two reactions in the tmRNA pathway that could be the target of small molecule inhibitors: the tagging of proteins by tmRNA, and the proteolysis of tagged proteins. This work targets both reactions to identify antibacterial compounds. Each reaction involves multiple components that could be disrupted. Inhibitors of tmRNA tagging may interfere with tmRNA itself or with SmpB, a protein cofactor required for tmRNA stability and activity Inhibitors of tmRNA may include molecules that block folding, processing, aminoacylation, or stability of tmRNA. SmpB is a small protein which binds specifically to tmRNA and is required for tmRNA association with the ribosome. Like tmRNA, SmpB is universally conserved in bacteria, and mutations in SmpB have the same phenotype as mutations in tmRNA. Inhibitors that block SmpB binding to tmRNA or to the ribosome should cause the tmRNA null phenotype. Inhibitors of general translation factors such as EF-Tu or the ribosome would also block tmRNA tagging activity, but the screen used in this project is designed to omit inhibitors of these factors because they are the targets of known antibiotics.

Several conserved proteases can degrade tmRNA-tagged proteins, but >90% of the degradation of cytoplasmic tagged proteins is accomplished by ClpXP. ClpXP is a multisubunit protease that is widely conserved in bacteria. The ClpX subunit is an ATPase responsible for recognition and unfolding of substrates, and the ClpP subunit contains the proteolytic active site. ClpXP activity is essential in *C. crescentus* and required for virulence in *Yersinia pseudotuberculosis* and *S typhimurium*, and homologs are required for virulence in *M. tuberculosis* and *Listeria monocytogenes*. ClpXP has a variety of substrates in addition to tmRNA-tagged proteins so inhibitors of ClpXP may result in phenotypes not associated with the tmRNA pathway. Nevertheless, the degradation of tmRNA-tagged proteins will be inhibited by molecules that block the active site of ClpP, that prevent substrate association with ClpX, or that interfere with the production or assembly of the ClpXP complex. In some cases, ClpXP recognition of tmRNA-tagged proteins is facilitated by a proteolysis specificity factor, SspB. SspB binds directly to the tmRNA-encoded peptide and to ClpX, tethering the substrate to the protease. However, SspB mutations have less severe phenotypes and SspB is not as highly conserved as other tmRNA pathway components.

Figure 2A:
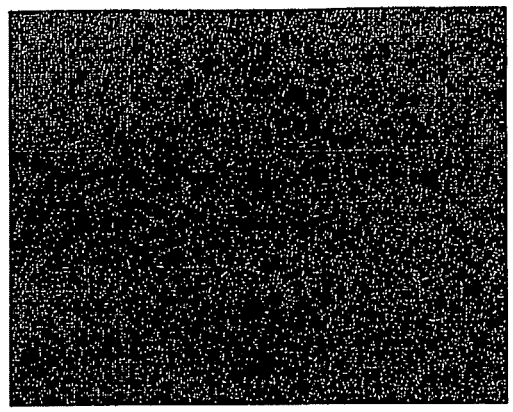
FIGS. 2A-2C are epifluorescence images showing the phenotype of cyclic peptide inhibitor in vivo. Wild type (FIG. 2A), clpX (B), and ICP1-producing E. coli strains bearing the GFP-tag reporter. Bright-field DIC and epifluorescence images were acquired and superimposed for each strain.
Figure 2B:
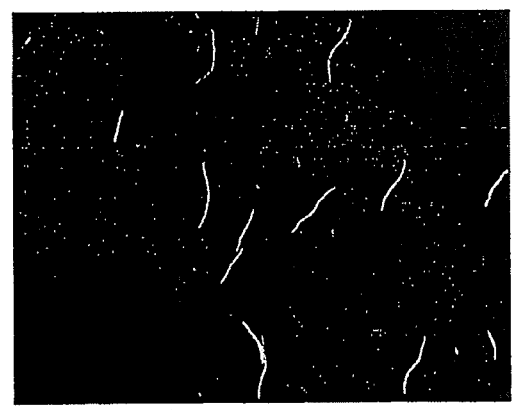
Figure 2C:
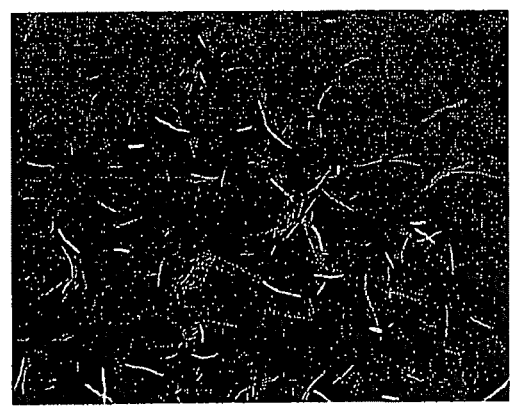

Cyclic peptides as lead compounds: Inhibitory compounds are selected from a library of randomized cyclic peptides. Cyclic peptides are ideal lead compounds because they are chemically complex and can engage in a wide array of interactions with proteins and nucleic acids; they can enter bacterial cells and are more stable in vivo than linear peptides; they are modular so combinatorial libraries can be constructed; and they contain multiple reactive side chains which facilitate chemical modification during late-stage drug development. Several natural antibiotics are cyclic peptides, including cyclosporin, polymyxins M and B, gramicidin S, and microcin J25. Cyclic peptides can be produced within bacterial cells, enabling the use of bacterial genetics in place of high-throughput in vitro screening for cyclic peptide inhibitors (Scott et al. (1999) Proc Natl Acad Sci USA 96, p 13638; Abel-Santos et al (2003) Methods Mol Biol 205, p 281). These references are incorporated herein in their entirety. This technology, termed Split Intein Circular Ligation of Proteins and Peptides (SICLOPPS), intein chemistry to produce cyclic peptides in bacteria (FIGS. 2A-2C). Inteins are sequence elements encoded in the DNA of an unrelated gene that splice themselves out of the protein after translation. These elements are analogous to self-splicing introns, but in the case of inteins splicing occurs in the protein instead of the mRNA. In bacteria the splicing of an intein out of a host protein is spontaneous, and depends on the interaction of domains at the N-terminal ($I_N$) and C-terminal ($I_C$) ends of the intein sequence. In the SICLOPPS technology, the relative positions of N-terminal ($I_N$) and C-terminal ($I_C$) are reversed, such that splicing will circularize the sequence inserted between the intein domains Because the reaction is spontaneous and is independent of the inserted sequence, any cyclic peptide can be produced in vivo. Cyclic peptides ranging in size from 5 to >150 amino acids have been produced by this method. Plasmids engineered to produce SICLOPPS proteins can be manipulated by standard genetic and molecular techniques. For example, libraries of cells expressing different cyclic peptides have been generated by randomization of codons for the internal sequence, and SICLOPPS libraries have been used to select inhibitors of protein-protein interactions. By using SICLOPPS libraries in conjunction with the screening methods described infra, $10^8$-$10^9$ peptides can be screened per day for inhibitors of the tmRNA pathway.

Linear peptides: In a preferred embodiment, the peptides can be cyclic or linear peptides. The linear peptides that are bactericidal also target the tmRNA tagged protein pathways. Treatments can include administering to a patient either cyclic peptides, linear peptides or a cocktail of both cyclic and linear peptides.

The linear peptides can be generated using plasmid libraries and tested as inhibitors of the tmRNA pathway as described herein. The linear peptides used to generate the cyclic peptides can also be used.

Alternative methods of producing linearized peptides and derivatives thereof include: chemically synthesis or synthesized using recombinant DNA techniques.

Procedure For Solid Phase Synthesis: Peptides may be prepared chemically by methods that are known in the art. For example, in brief, solid phase peptide synthesis consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, J. Am. Chem. Soc. 85:2149; Vale et al., 1981, Science 213:1394 1397; Marki et al., 1981, J. Am. Chem. Soc. 103:3178 and in U.S. Pat. Nos. 4,305,872 and 4,316,891. In a preferred aspect, an automated peptide synthesizer is employed. By way of example but not limitation, peptides can be synthesized on an Applied Biosystems Inc. ("ABI") model 431A automated peptide synthesizer using the "Fastmoc" synthesis protocol supplied by ABI, which uses 2-(1H-Benzotriazol-1-yl)-1,1,3,3-tetramethyluronium hexafluorophosphate ("HBTU") (R. Knorr et al., 1989, Tet. Lett., 30:1927) as coupling agent. Syntheses can be carried out on 0.25 mmol of commercially available 4-(2',4'-dimethoxyphenyl-(9-fluorenyl-methoxycarbonyl)-aminomethyl)-phenoxy polystyrene resin ("Rink resin" from Advanced ChemTech) (H. Rink, 1987, Tet. Lett. 28:3787). Fmoc amino acids (1 mmol) are coupled according to the Fastmoc protocol. The following side chain protected Fmoc amino acid derivatives are used: FmocArg (Pmc)OH; FmocAsn(Mbh)OH; FmocAsp(tBu)OH; Fmoc-Cys(Acm)OH; FmocGlu(tBu)OH; FmocGln(Mbh)OH; FmocHis(Tr)OH; FmocLys(Boc)OH; FmocSer(tBu)OH; FmocThr(tBu)OH; FmocTyr(tBu)OH. [Abbreviations: Acm, acetamidomethyl; Boc, tert-butoxycarbonyl; tBu, tert-butyl; Fmoc, 9-fluorenylmethoxycarbonyl; Mbh, 4,4'-dimethoxybenzhydryl; Pmc, 2,2,5,7,8-pentamethylchroman-6-sulfonyl; Tr, trityl].

Synthesis is carried out using N-methylpyrrolidone (NMP) as solvent, with HBTU dissolved in N,N-dimethylformamide (DMF). Deprotection of the Fmoc group is effected using approximately 20% piperidine in NMP. At the end of each synthesis the amount of peptide present is assayed by ultraviolet spectroscopy. A sample of dry peptide resin (about 3 10 mg) is weighed, then 20% piperidine in DMA (10 ml) is added. After 30 min sonication, the UV (ultraviolet) absorbance of the dibenzofulvene-piperidine adduct (formed by cleavage of the N-terminal Fmoc group) is recorded at 301 nm. Finally, the N-terminal Fmoc group is cleaved using 20% piperidine in DMA, then acetylated using acetic anhydride and pyridine in DMA. The peptide resin is thoroughly washed with DMA, $CH_2Cl_2$ and finally diethyl ether.

By way of example but not limitation, cleavage and deprotection can be carried out as follows: The air-dried peptide resin is treated with ethylmethyl-sulfide (EtSMe), ethanedithiol (EDT), and thioanisole (PhSMe) for approximately 20 min. prior to addition of 95% aqueous trifluoracetic acid (TFA). A total volume of approximately 50 ml of these reagents per gram of peptide-resin is used. The following ratio is used: TFA:EtSMe:EDT:PhSMe (10:0.5:0.5:0.5). The mixture is stirred for 3 h at room temperature under an atmosphere of $N_2$. The mixture is 30 filtered and the resin washed with TFA (2.times.3 ml). The combined filtrate is evaporated in vacuo, and anhydrous diethyl ether added to the yellow/orange residue. The resulting white precipitate is isolated by filtration. See King et al., 1990, Int. J. Peptide Protein Res. 36:255 266 regarding various cleavage methods.

Purification of the synthesized peptides can be carried out by standard methods including chromatography (e.g., ion exchange, affinity, and sizing column chromatography, high performance liquid chromatography (HPLC)), centrifugation, differential solubility, or by any other standard technique.

Biowarfare defense: The threat of biological attacks using anthrax, drug-resistant pathogens, or unknown pathogens grows with the proliferation of biowarfare agents and microbiological expertise. In addition, troop preparedness and performance is challenged by disease caused by known and unknown pathogens. The development of new classes of antibiotics that can be used to treat a broad spectrum of pathogens is crucial to combat the rise of drug-resistant bacteria. Antibiotic compounds are identified that can be used to kill pathogenic bacteria directly, or that can be used to eliminate plasmids carrying virulence factors or drug resistance genes so that conventional antibiotics are effective.

Potency tests will be conducted on panels of pathogens and model systems for pathogens. These organisms include potential biowarfare agents such as *B. anthracis*, species of *Francisella, Yersinia, Burkholderia, Bordetella, Brucella, Rickettsia, Shigella, Campylobacter, Listeria, Vibrio, Salmonella*, and pathogenic strains of *E. coli*. In addition, many of the bacteria listed above have a significant impact on troop preparedness. *Neisseria meningitides* and *Acinetobacter baumannii*, which negatively impact troop preparedness, will also be tested. Because the tmRNA pathway is ubiquitous in bacteria, the inhibitors found in this work may have broad species specificity, allowing their use before the precise identity of the bacterial agent is known. This application would be especially useful in situations where intelligence and medical evidence are not sufficient to determine the bacterial agent. Further technologies described herein can be generalized for antibiotic development from other libraries and against other molecular targets.

Public Purpose: Other uses include substantial benefit to the public as well as the military, because the underlying problems of pathogen exposure and spread of antibiotic resistance in bacteria are very similar. The civilian sector faces threats of intentional exposure to pathogenic bacteria from enemy military and terrorist sources, as well as emergent pathogens. In addition, there is a certain challenge to public health posed by the spread of antibiotic resistance to pathogens that can currently be treated with conventional antibiotics. Novel compounds are produced that can be used to kill a wide spectrum of bacteria, and compounds that eliminate plasmids that carry drug resistance and virulence genes. These compounds could be used alone or in combination with conventional antibiotics to improve public health.

Bacterial Diseases

Bacterial infections: According to preferred embodiments of the invention, the cyclic peptides are used to treat human or domestic animal bacterial diseases. Examples of pathogens, other than those discussed infra, are listed in (but not restricted to) table 1. The tmRNA can be tagged to molecular targets which may include (but are not restricted to) gene products essential to bacterial survival and multiplication in the host organism, virulence gene products encoding single- or multi-drug resistance such as for instance the gene products listed in table 2.

TABLE 1

Selected bacteria causing serious human diseases

| | |
|---|---|
| Gram positive organisms: | *Staphylococcus aureus*: strains include methicillin resistant (MRSA), methicillin-vancomycin resistant (VMRSA) and vancomycin intermediate resistant (VISA). |
| | *Staphylococcus epidermidis*. |
| | *Enterococcus faecalis* and *E. faecium*: strains include vancomycin resistant (VRE). |
| | *Streptococcus pneumoniae*. |
| Gram negative organisms: | *Pseudomonas aeruginosa*. |
| | *Burkholdia cepacia*. |
| | *Xanthomonas maltophila*. |
| | *Escherichia coli* |
| | *Enterobacter* spp. |
| | *Klebsiella pneumoniae* |
| | *Salmonella* spp. |

References: Cookson B. D., Nosocomial antimicrobial resistance surveillance. J. Hosp. Infect. 1999:97-103. Richards M. J. et al. Nosocomial infections in medical intensive care units in the United States. National Nosocomial Infections Surveillance System. Crit. Care. Med. 1999; 5:887-92. House of Lords Select Committee on Science and Technology. Resistance to antibiotics and other antimicrobial agents. London: 1998; Her Majesty's Stationary Office. Johnson A. P. Intermediate vancomycin resistance in *S. aureus*: a major threat or a minor inconveniance? J. Antimicrobial. Chemother. 1998; 42:289-91. Baquero F. Pneumococcal resistance to beta-lactam antibiotics: a global overview. Microb. Drug Resist. 1995; 1:115-20. Hsueh P. R. et al. Persistence of a multidrug resistant *Pseudomonas aeruginosa* clone in an intensive care burn unit. J. Clin. Microbiol. 1998; 36:1347-51. Livermore D. Multiresistance and Super-bugs. Commun. Dis. Public Health 1998; 1:74-76.

Some preferred target s in bacteria would include (but are not restricted to) molecules involved in the following biological functions: 1. Protein synthesis; 2. Cell wall synthesis; 3: Cell division; 4: Nucleic acid synthesis; and 5: Virulence. The biological functions mentioned are analogous in Gram positive and Gram negative bacteria, and the genes encoding the individual proteins involved may exhibit extensive homologies in their nucleotide sequences. The genes encoding the mentioned target complexes may have different names in different bacteria.

TABLE 2

Examples of selected target complexes in bacteria.

| | |
|---|---|
| Protein synthesis | Translation initiation factors (e.g. IF1, IF2, IF3) |

TABLE 2-continued

Examples of selected target complexes in bacteria.

| | |
|---|---|
| targets | Translation elongation factors (e.g. EF-Tu, EF-G) |
| | Translation release factors (RF1, RF2, RF3) |
| Cell wall synthesis | Penicillin binding proteins (e.g. PB.P.1 to PB.P.9) |
| Cell division | Proteins encoded by the ftsQAZ operon |
| Nucleic acid synthesis | Gyrases, Sigma 70 and Helicase |
| Virulence | Ureases |

References: *Escherichia coli* and *Salmonella* in Cellular and Molecular Biology, vol 1 & 2. C Neidhardt and R Curtiss (eds.), American Society for Microbiology Press. Gram-Positive Pathogens. V A Fischetti et al. (eds.), American Society for Microbiology Press. Bacterial Pathogene productsis: A Molecular Approach. A A Salyers and D D Whitt (eds.), American Society for Microbiology Press. Organization of the Procaryotic Genome. R L Charlebois (ed.), American Society for Microbiology Press.

Listed in Table 3 below are examples of genes encoding the protein complexes listed in Table 2 above. The individual genes have homologues in the major human pathogenic bacteria listed in Table 1. Table 3 below depicts an example of a Gram negative (*Escherichia coli*) and a Gram positive (*Staphylococcus aureus*) organism, chosen as representatives for the two groups of bacteria.

TABLE 3

Examples of gene products encoding possible tmRNA target proteins.

| Target group | E. coli | S. aureus |
|---|---|---|
| Protein synthesis | prfA | prfA |
| | prfB | |
| | prfC | prfC |
| | infA | infA |
| | infB | infB |
| | infC | |
| | tufA | tuf |
| | fusA | fus |
| Cell wall synthesis | mrcA | pbpA |
| | mrcB | pbp2 |
| | pb.p.B | fmhB |
| | | femA |
| | | femftsAB |
| Cell division | ftsA | |
| | ftsQ | |
| | ftsZ | ftsZ |
| Nucleic acid synthesis | gyrA | pcrC |
| | gyrB | |
| | rpoD | |

References: *Escherichia coli* and *Salmonella* in Cellular and Molecular Biology, vol 1 & 2. C Neidhardt and R Curtiss (eds.), American Society for Microbiology Press. Gram-Positive Pathogens. V A Fischetti et al. (eds.), American Society for Microbiology Press. Bacterial Pathogenesis: A Molecular Approach. A A Salyers and D D Whitt (eds.), American Society for Microbiology Press. Organization of the Prokaryotic Genome. R L Charlebois (ed.), American Society for Microbiology Press.

It should be appreciated that in the above Tables 2 and 3, an indicated gene means the gene and all currently known variants thereof, including the different mRNA transcripts that the gene and its variants can give rise to, and any further gene variants which may be elucidated. In general, however, such variants will have significant sequence identity to a sequence of Tables 2 and 3 above, e.g. a variant will have at least about 70 percent sequence identity to a sequence of the above Tables 2 and 3, more typically at least about 75, 80, 85, 90, 95, 97, 98 or 99 percent sequence identity to a sequence of the above Tables 2 and 3. Sequence identity of a variant can be determined by any number of standard techniques such as a BLAST program (ncbi.nlm.nih.gov/blast/).

Sequences for the gene products listed in Tables 2 and 3 can be found in GenBank (ncbi.nlm.nih.gov/). The gene sequences may be genomic, cDNA, or mRNA sequences.

Chimeric/Modified Cyclic Peptide Nucleic Acid Sequences, Amino Acids and Peptides Cyclic peptides identified as inhibitors of the pathways of tmRNA may have their amino acid residues and sequences further modified to provide cyclic peptides with higher affinities for molecular targets, stability etc.

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls, as well as any other amino acid analog.

The term amino acid residue further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the peptides can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention can include asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

In some aspects, the amino acids comprise protecting groups. The phrase "protecting group" as used herein means substituents which protect the reactive functional group from undesirable chemical reactions. Examples of such protecting groups include esters of carboxylic acids and boronic acids, ethers of alcohols and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (FMOC).

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an acetyl group, or the like. Specific examples of unnatural amino acids include, but are not limited to, O-methyl-L-tyrosine, an L-3-(2-naphthyl) alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. Examples of L-asparagine and L-aspartic acid analogs, include but not limited to 5-carboxamido-4-amino-3-isoxazolidone and N-substituted sulfonamides. N'-substituted sulfonylhydrazides have been prepared as sulfur analogues of L-asparagine.

Typically, the unnatural amino acids of the invention are selected or designed to provide additional characteristics unavailable in the twenty natural amino acids. For example, unnatural amino acid are optionally designed or selected to modify the biological properties of a protein, e.g., into which they are incorporated. For example, the following properties are optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Many of the unnatural amino acids provided above are commercially available, e.g., from Sigma (USA) or Aldrich (Milwaukee, Wis., USA). Those that are not commercially available are optionally synthesized as provided in the examples below or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York).

Modified peptide backbones are also included within the scope of the invention. An example of a useful nucleic acid analogue is the peptide nucleic acid (PNA), in which standard DNA bases are attached to a modified peptide backbone comprised of repeating N-(2-aminoethyl)glycine units (Nielsen et al., Science 254:1497-1500 (1991)). The peptide backbone is capable of holding the bases at the proper distance to facilitate hybridization with conventional DNA and RNA single strands. PNA-DNA hybrid duplexes are much stronger than otherwise equivalent DNA-DNA duplexes, probably due to the fact that there are no negatively charged phosphodiester linkages in the PNA strand. In addition, because of their unusual structure, PNAs are very resistant to nuclease degradation.

The linker itself can consist of many different components, each having a characteristic property offering a unique advantage. One skilled in the art of organic synthesis could design and synthesize a great variety of linkers having the required chemical functionality to join the nucleic acid to the first polymerizable ethylene-containing monomer unit. Examples of different linkers which can be used in the present invention include, for example: peptide chains, carbohydrate chains, poly(ethylene glycol), poly(vinyl alcohol), and poly(vinyl pyrrolidone). This listing is by no means comprehensive, a wide array of appropriate linkers can be designed and synthesized through the application of routine experimentation (Sandler and Karo, Polymer Synthesis Vol. 1, Academic Press, Inc. (1992); Sandler and Karo, Polymer Synthesis Vol. 2, Academic Press, Inc. (1994)).

In some instances, an assay may require a linker which can be cleaved to release the nucleic acid molecule from its attachment to the ethylene-containing monomer unit. There are several types of cleavable linkers which are appropriate for such an application, many of which are readily available from commercial sources. Such linkers can be cleaved, for example, chemically, enzymatically, thermally or by exposure to light. For example, linkers containing disulfide bonds are sensitive to chemical cleavage (Mattson et al., Molecular Biology Reports 17:167-183 (1993)). Exposure of such a linker to a reducing agent such as β-mercaptoethanol or dithiothreitol, results in the cleavage of the disulfide bond. Linkers formed from either carbohydrates or peptides can be sensitive to cleavage by enzymatic means. Thermally sensitive and photocleavable linkers offer alternatives to the chemical or enzyme sensitive linkers, however, their use is not compatible with all methods of polymerization. For example, thermal induction of polymerization would result in cleavage of a linker sensitive to heat.

Cyclic peptides identified as inhibitors of the pathways of tmRNA may have their nucleic acid coding sequences further modified to provide cyclic peptides with higher affinities for molecular targets, stability etc. Thus, oligonucleotides may be formulated in accordance with this invention which are targeted wholly or in part to these associated ribonucleotides as well as to the coding ribonucleotides.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties Specific examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, —$N(CH_3)$—O—$CH_2$ [known as a methylene (methylimino) or MMI backbone], $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones, wherein the native phosphodiester backbone is represented as O—P—O—$CH_2$). The amide backbones disclosed by De Mesmaeker et al. Acc. Chem. Res. 1995, 28:366-374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. Science 1991, 254, 1497). Oligonucleotides may also comprise one or more substituted sugar moieties. Preferred oligonucleotides comprise one of the following at the 2' position: OH, SH, $SCH_3$, F, OCN, $OCH_3$ $OCH_3$, $OCH_3O$ $(CH_2)_nCH_3$, $O(CH_2)_2NH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl)] (Martin et al., Helv. Chim. Acta, 1995, 78, 486). Other preferred modifications include 2'-methoxy(2'-G-CH$_3$), 2'-propoxy(2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N$_6$(6-aminohexyl)adenine and 2,6-diaminopurine. Kornberg, A., DNA Replication, W.H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA 1989, 86, 6553), cholic acid (Manoharan et al. Bioorg. Med. Chem. Let. 1994, 4, 1053), a thioether, e.g., hexyl-5-tritylthiol (Manoharan et al. Ann. N.Y. Acad. Sci. 1992, 660, 306; Manoharan et al. Bioorg. Med. Chem. Let. 1993, 3, 2765), a thiocholesterol (Oberhauser et al., Nucl. Acids Res. 1992, 20, 533), an aliphatic chain, e.g., dodecandiol or undecyl residues (Saison-Behmoaras et al. EMBO J. 1991, 10, 111; Kabanov et al. FEBS Lett. 1990, 259, 327; Svinarchuk et al. Biochimie 1993, 75, 49), a phospholipid, e.g., di-hexadecyl-rac-glycerol or triethylammonium 1,2-di-O-hexadecyl-rac-glycero-3-H-phosphonate (Manoharan et al. Tetrahedron Lett. 1995, 36, 3651; Shea et al. Nucl. Acids Res. 1990, 18, 3777), a polyamine or a polyethylene glycol chain (Manoharan et al. Nucleosides & Nucleotides 1995, 14, 969), or adamantane acetic acid (Manoharan et al. Tetrahedron Lett. 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc (ref: Recent advances in the medical chemistry of antisense oligonucleotide by Uhlman, Current Opinions in Drug Discovery & Development 2000 Vol 3 No 2). This can be achieved by substituting some of the monomers in the current oligonucleotides by LNA monomers. The LNA modified oligonucleotide may have a size similar to the parent compound or may be larger or preferably smaller It is preferred that such LNA-modified oligonucleotides contain less than about 70%, more preferably less than about 60%, most preferably less than about 50% LNA monomers and that their sizes are between about 10 and 25 nucleotides, more preferably between about 12 and 20 nucleotides.

Administration of Compositions

The pharmaceutical compositions of the invention may be administered to animals including humans in any suitable formulation. For example, the compositions may be formulated in pharmaceutically acceptable carriers or diluents such as physiological saline or a buffered salt solution. Suitable carriers and diluents can be selected on the basis of mode and route of administration and standard pharmaceutical practice. A description of other exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions, or enhance the activity of the Msr system. One such enhancing substance could be nicotinamide which is part of the molecule, NADPH, that supplies the reducing power to the reaction catalyzed by the members of the Msr family.

The compositions of the invention may be administered to animals by any conventional technique. Such administration may be oral or parenteral (for example, by intravenous, subcutaneous, intramuscular, or intraperitoneal introduction). The compositions may also be administered directly to the target site by, for example, surgical delivery to an internal or external target site, or by catheter to a site accessible by a blood vessel. Other methods of delivery, for example, liposomal delivery or diffusion from a device impregnated with the composition, are known in the art. The compositions may be administered in a single bolus, multiple injections, or by continuous infusion (for example, intravenously or by peritoneal dialysis). For parenteral administration, the compositions are preferably formulated in a sterilized pyrogen-free form.

Compositions of the invention can also be administered in vitro to a cell (for example, to prevent oxidative damage during ex vivo cell manipulation, for example of organs used for organ transplantation or in in vitro assays) by simply adding the composition to the fluid in which the cell is contained.

Effective Doses

An effective amount is an amount which is capable of producing a desirable result in a treated animal or cell (for example, reduction of bacterial numbers, bactericidal etc). As is well known in the medical and veterinary arts, dosage for any one animal depends on many factors, including the particular animal's size, body surface area, age, the particular composition to be administered, time and route of administration, general health, and other drugs being administered concurrently. It is expected that an appropriate dosage for parenteral or oral administration of compositions of the invention would be in the range of about 0.001 µg to 100 mg/kg of body weight in humans An effective amount for use with a cell in culture will also vary, but can be readily determined empirically (for example, by adding varying concentrations to the cell and selecting the concentration that best produces the desired result). It is expected that an appropriate concentration would be in the range of about 0.0001-100 mM. More specific dosages can be determined by the method described below.

Toxicity and efficacy of the compositions of the invention can be determined by standard pharmaceutical procedures, using cells in culture and/or experimental animals to determine the $LD_{50}$ (the dose lethal to 50% of the population) and the $ED_{50}$ (the dose that effects the desired result in 50% of the population). Compositions that exhibit a large $LD_{50}/ED_{50}$ ratio are preferred. Although less toxic compositions are generally preferred, more toxic compositions may sometimes be used in in vivo applications if appropriate steps are taken to minimize the toxic side effects.

Data obtained from cell culture and animal studies can be used in estimating an appropriate dose range for use in humans. A preferred dosage range is one that results in circulating concentrations of the composition that cause little or no toxicity. The dosage may vary within this range depending on the form of the composition employed and the method of administration.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1

Selection of tmRNA Inhibitors as Antibacterial and Plasmid Elimination Agents

The experimental strategy for this proposal is to engineer fluorescent reporters for the tmRNA pathway and conduct a genetic screen for inhibitors from libraries of cyclic peptides expressed in vivo Inhibitors will be optimized by mutagenesis followed by re-screening for high-affinity inhibitors in model organisms. Initial characterization will be performed on opportunistic pathogens and model bacteria that can be handled under BL1 and BL2 conditions in the laboratory. Optimal cyclic peptides will then be tested for antibiotic and plasmid elimination activity against B. anthracis and an array of bacterial pathogens. A pilot genetic screen and characterization of ClpXP inhibitors has been performed to validate key methods.

Development of reporters for the tmRNA pathway: To probe the activity of the tmRNA pathway, fluorescent reporters will be developed for tmRNA activity and proteolysis of tagged proteins by ClpXP protease. A reporter for tmRNA activity will be constructed by targeting the yellow fluorescent protein, EYFP, to the tmRNA pathway. This reporter will probe all steps of the pathway and can be used to identify inhibitors of tmRNA tagging and degradation of tagged proteins. An eyfp gene that produces mRNA with no stop codon will be engineered by inserting a strong transcriptional terminator before the stop codon. Identical mutations in other genes have been shown to produce proteins tagged by tmRNA. This eyfp-trAt gene will be placed under the control of the IPTG-inducible promoter Ptrc, and integrated into a neutral locus of the *E. coli* K12 chromosome. When the tmRNA pathway is functional, the EYFP-trpAt protein should be tagged by tmRNA and degraded by ClpXP, resulting in no accumulation of EYFP and no yellow fluorescence. However, if any step in the tmRNA pathway is blocked, the EYFP-trpAt protein should accumulate and produce yellow fluorescence within the cells. This behavior will be verified by ensuring that in wild-type *E. coli* K12 expressing EYFP-trpAt there is little fluorescence, but in an isogenic strain deleted for tmRNA there is significant yellow fluorescence Inhibitors that block any essential step in the tmRNA pathway will result in accumulation of EYFP from this reporter and produce yellow fluorescence in the cells.

A second reporter, specific for the proteolysis of tmRNA-tagged proteins by ClpXP, has been generated, for use in pilot experiments. For this reporter, EGFP (enhanced green fluorescent protein) was targeted to ClpXP by adding codons for the 11 residue tmRNA peptide to the 3' end of the egfp gene. Although the protein (EGFP-tag) made from this gene will not be targeted to the tmRNA pathway, it will all have the tmRNA peptide tag at the C terminus. A plasmid-borne version of this reporter (pEGFP-tag) was made by cloning egfp-tag under the control of the IPTG-inducible Ptrc promoter in a high copy number plasmid. Preliminary results demonstrate that the EGFP-tag protein made from pEGFP-tag is rapidly degraded in vivo and in vitro by ClpXP. Furthermore, wild-type *E. coli* bearing the pEGFP-tag reporter plasmid are not fluorescent even when expression of egfp-tag is induced by adding IPTG to the culture. Two controls indicate that proteolysis of EGFP-tag is through the normal tmRNA-ClpXP pathway. First, EGFP-tag is not degraded in a strain that is deleted for the clpX gene, and the cells are highly fluorescent when IPTG is added. Second, mutations known to disrupt the degradation of tmRNA-tagged proteins were made in the pEGFP-tag plasmid, and these mutations eliminate proteolysis of EGFP-tag. Changing the codons for the C-terminal amino acids in the tmRNA tag sequence from AA to DD is known to prevent degradation by ClpXP. When the terminal amino acids in pEGFP-tag were changed to DD, the resulting protein was stable and fluorescent in wild-type *E. coli*, and was not degraded by ClpXP in vitro. Therefore, the EGFP-tag reporter is degraded through the normal tmRNA-ClpXP pathway. As described below, pEGFP-tag has been successfully employed to select inhibitors of ClpXP. These experiments have demonstrated that the strategy for generating fluorescent reporters for the tmRNA pathway is effective.

It is possible that screening for tmRNA pathway inhibitors with the EYFP-trpAt reporter will preferentially yield inhibitors of tmRNA tagging, or of degradation of tagged proteins. If few inhibitors of degradation of tmRNA-tagged proteins are obtained from the EYFP-trpAt screen, a complete screen with EGFP-tag will be executed. To facilitate optimization and screening techniques, the EGFP-tag reporter will be integrated into a neutral locus of the *E. coli* K12 chromosome. Conversely, if the EYFP-trpAt screen is dominated by ClpXP inhibitors, inhibitors of tmRNA tagging will be selected using a strain with both the EYFP-trpAt and EGFP-tag reporters integrated into the chromosome. Because the fluorescence emission wavelengths for EGFP and EYFP are distinguishable, these reporters can be used in combination to identify inhibitors that target tmRNA but not ClpXP. A strain producing EGFP-tag and EYFP-trpAt will be fluorescent at green and yellow wavelengths in the presence of a ClpXP inhibitor because degradation of both reporter proteins will be blocked. In the presence of an inhibitor of tmRNA tagging, the EGFP-tag will be degraded but the tagging of EYPF-trpAt will be blocked, resulting in fluorescence at yellow wavelengths but not at green wavelengths. Cells with yellow fluorescence but no green fluorescence can be selected by FACS as described below. Therefore, the EYFP-trpAt and EGFP-tag reporters will enable selection of inhibitors of all reactions in the tmRNA pathway.

Construction of cyclic peptide library: Cyclic peptide inhibitors of tmRNA will be selected from a library of randomized peptides expressed in vivo using SICLOPPS. Four residues at the splicing junction will be fixed to optimize the efficiency of circular ligation, but other residues in the peptide will be randomized. SICLOPPS vectors have been constructed with restriction sites between the $I_C$ and $I_N$ sequences so that the sequence encoding the cyclic peptide can be easily inserted. Oligonucleotide cassettes are synthesized to encode the desired number of randomized codons, flanked by codons for the fixed cyclic peptide residues and restriction sites, and the cassettes are ligated into the SICLOPPS vector. The randomized codons are specified as NN(G/C), allowing any base to be incorporated at the first two positions, and either G or C at the third position. This base composition will encode all 20 amino acids, but provides a more even weighting of amino acids than an NNN codon, and reduces the probability of encoding a stop codon. The incorporation of randomized codons is verified by DNA sequencing. Each SICLOPPS library is carried on a pACYC plasmid, and the cyclic peptide gene is expressed from an arabinose-inducible promoter. Libraries of cyclic peptides have been constructed in this fashion in which 5 and 7 residues are randomized, and these libraries are named by the number of randomized amino acids: SICLOPPS($X_5$) and SICLOPPS($X_7$). The SICLOPPS($X_5$) library theoretically contains $3.4 \times 10^7$ DNA sequences that encode $3.2 \times 10^6$ different cyclic peptides, and the SICLOPPS ($X_7$) library theoretically contains $3.4 \times 10^{10}$ DNA sequences that encode $1.3 \times 10^9$ different cyclic peptides.

Selection of tmRNA pathway inhibitors by FACS: Inhibitors of the tmRNA pathway will be selected based on fluorescence from the tmRNA pathway reporters using Fluorescence Activated Cell Sorting (FACS). FACS enables the isolation of individual cells with the desired fluorescence from a large heterogeneous population. FACS has several advantages for selection of lead compounds: 1) more than $10^8$ cells can be sorted per hour; 2) the selection criteria are tunable, allowing isolation of moderately to highly active inhibitors during initial selection and highly active inhibitors during optimization; 3) multiple fluorescent reporters can be used during the same sort, allowing selection of inhibitors with the desired combination of properties. Pilot experiments using EGFP-tag have demonstrated that this strategy works and is highly effective.

To select inhibitors of the tmRNA pathway, the EYFP-trpAt reporter strain will be transformed with one of the SICLOPPS libraries and the expression of the cyclic peptides and EYFP-trpAt will be induced by addition of IPTG and arabinose to the culture medium. Cells will be sorted by FACS to isolate those with the highest fluorescence intensity. Based on pilot experiments described below, those cells brighter than 99.99999% of the population (1 in $10^7$) will be selected by the flow cytometer and deposited individually on agar plates using the AutoClone flow cytometer attachment (Coulter) to allow clonal growth. Sorting $10^9$ cells should take about 4 hours and result in 100 colonies of cells containing a cyclic peptide inhibitor.

To eliminate false positives and focus on the most efficient inhibitors, several filtering steps will be conducted after the FACS screen. First, to ensure that the observed fluorescence is due to the cyclic peptide and not to a spontaneous mutation in the reporter plasmid or chromosome, the SICLOPPS plasmid will be prepared from cells in each colony and transformed into naive EYFP-trpAt reporter cells. These freshly transformed cells will then be assayed for the intensity and penetrance of the fluorescent phenotype to ensure that this phenotype in conferred by the SICLOPPS plasmid. Expression of the cyclic peptide and reporter will be induced by addition of IPTG and arabinose, and the fluorescence intensity of each cell will be measured by epifluorescence microscopy using ImagePro software. This software can measure the fluorescence intensity of all cells in the microscope field (100-300) simultaneously. Stochastic variations in gene expression will result in a distribution of intensities, but a potent inhibitor should produce high fluorescence in most cells in the population. More than 1000 cells will be measured to determine the average fluorescence and the percentage of cells with fluorescence above background. SICLOPPS plasmids that result in the highest fluorescence intensity and have at least 75% of the population above background will be selected for the optimization round. The composition of the cyclic peptide produced by each plasmid will be determined by DNA sequencing.

A pilot screen has been conducted to validate the FACS and epifluorescence methods by isolating inhibitors of ClpXP using the pEGFP-tag reporter. The SICLOPPS($X_5$) library was transformed into *E. coli* with the pEGFP-tag reporter and plated on selective medium. The colonies were pooled and the brightest 0.01% were selected by FACS. A liberal fluorescence intensity cutoff was used in this sort to ensure that enough viable colonies were obtained to assess the epifluorescence methods. In fact, almost all of the cells survived the FACS and produced colonies, so a much more restrictive cutoff can be used for future sorts. After preparation of the SICLOPPS plasmids from >200 colonies and transformation into naive E. coli with pEGFP-tag, 30% of plasmids produced little fluorescence or resulted in <75% bright cells in the epifluorescence analysis. Of the remaining SICLOPPS plasmids, 8 produced significantly higher fluorescence intensity and were chosen for further characterization. As described below, the cyclic peptides produced by these plasmids inhibit ClpXP in vitro. Furthermore, as shown below, these cyclic peptides kill the model bacteria C. crescentus and B. subtilis when added exogenously. Therefore, the screen described here can produce bona fide inhibitors of the tmRNA pathway, and these inhibitors have antibiotic activity.

It is possible that screening with the EYFP-trpAt reporter will produce predominantly inhibitors of ClpXP and few inhibitors of other steps in the tmRNA pathway. If this is the case, inhibitors of tmRNA tagging will be identified by simultaneously selecting tmRNA pathway inhibitors and counter-selecting for ClpXP inhibitors. The FACS selection will be repeated with a strain containing both the EFGP-tag and EYFP-trpAt reporters, and cells with the brightest yellow fluorescence but low green fluorescence will be selected. The exact parameters for yellow and green fluorescence will be determined empirically using trial sorts.

Optimization: Because transformation and FACS screening of libraries is practical up to $10^9$ cells, almost all of the $10^7$ DNA sequences present in the SICLOPPS($X_5$) library will be screened. However, for the SICLOPPS($X_7$) library many sequences will not be present in the screened pool, and optimization of the selected inhibitor sequences will be crucial. Because the optimization strategy described below is fast, cheap, and technically easy to perform, it will be used for cyclic peptides selected from all libraries to ensure that the optimal inhibitors are obtained. Bacterial genetics provides an efficient means to search for sequences that are closely related to selected inhibitors that have increased inhibitory activity. Clonal populations of cells selected by FACS will be grown in liquid culture and mutagenized by the addition of ethyl methane sulfonate (EMS). Cells with the mutagenized SICLOPPS plasmids will be subjected to another round of FACS using a cutoff at higher fluorescence than the original sort to isolate those with increased inhibition. Although it is possible that EMS mutagenesis may introduce changes in the chromosomal DNA that affect fluorescence, these false positives will be eliminated by preparing the selected mutagenized SICLOPPS plasmids, transforming them into naive reporter cells, and repeating the epifluorescence screening steps as described above. Plasmids that confer the highest fluorescence in naive reporter cells will be retained.

If a sufficient degree of mutagenesis can not be obtained by EMS treatment, site-directed mutagenesis of individual residues or pairs of residues will be used to examine sequences closely related to those selected by the initial screen. One or two codons within the cyclic peptide reading frame will be randomized by PCR using degenerate oligonucleotides. Mutagenized peptides will be assayed for increased inhibition by FACS as described above. The entire sequence space for two randomized residues can be scanned by analyzing 10,000 cells by FACS, so all 10 pairings of residues in a 9-mer sequence could be readily analyzed. Although this mutagenesis provides a thorough coverage of the local sequence space around a given cyclic peptide sequence, it is less efficient than chemical mutagenesis and will only be pursued as a backup strategy.

Inhibitor purification: Purified cyclic peptides must be obtained to test the antibiotic efficacy and to determine the molecular targets of these inhibitors. Cyclic peptides can be produced from synthetic linear peptides by immobilizing the peptide on a disulfide resin and incubating the immobilized peptide with 1-ethyl-3-(3'-dimethylaminopropyl)carbodiimide and 1-hydroxy-7-azabenzotriazole. The products are cleaved from the resin and the cyclic peptide is purified by reverse-phase HPLC. This method has been used to produce milligram quantities of cyclic peptide (Horswill et al. (2004) Proc Natl Acad Sci USA 101, p. 15591) and will be used for initial characterization.

If larger quantities of cyclic peptides are required, the peptides will be produced by purifying the unspliced SICLOPPS proteins from bacterial cultures and allowing the circular ligation reaction to proceed in vitro. Split intein proteins with the desired peptide sequence will be overproduced in E. coli by expression from a T7 promoter at 15° C. The low temperature reduces splicing of the cyclic peptide in vivo. The split intein proteins will be purified by affinity chromatography at 4° C. to inhibit splicing, and the purified protein will be incubated at 37° C. for 16 h to allow cyclization. The cyclic peptide will be purified away from the intein fragments by reverse-phase HPLC. Trial purifications have yielded pure cyclic peptide inhibitors of ClpXP that have the same activity in vitro as the chemically synthesized versions.

Antibiotic activity: The antibiotic activity of purified cyclic peptides will be assayed using standard laboratory control microorganisms to identify candidates for testing on select agents. Testing on select agents will be performed. Initial assays will be performed on opportunistic pathogens and model bacteria that can be handled under BL1 and BL2 conditions in the laboratory. These assays will ensure that inhibitory cyclic peptides can enter and kill cells. The bacteria to be tested in the lab are listed below. Model bacteria are listed with the corresponding closely-related pathogens, and opportunistic pathogens with the corresponding disease.

| bacterium to be tested | related pathogen (disease) |
| --- | --- |
| B. subtilis | B. anthracis (anthrax) |
| C. crescentus | Brucella (brucellosis), Ricketisia (vasculitis) |
| Yersinia pseudotuberculosis | Yersinia pestis (plague) |
| Bordetella bronchiseptica | Burkholderia mallei (glanders) and Bordetella pertussis (pertussis toxin) |
| Moraxella catarrhalis | Acinetobacter baumannii (blood infections) |
| E. coil K12 | Fracisella tularensis (tularemia) |
| S. flexneri | (shigellosis) |
| Enteroinvasive E. coli (EIEC) | (dysentery) |
| S. typhimurium | (food poisoning) |

The minimum inhibitory concentration (MIC) for each cyclic peptide will be determined using broth dilution assays in microtiter plates, and the minimum bactericidal concentration (MBC) will be determined using agar plating assays. Cyclic peptides that effectively kill B subtilis (MIC<1 µg/ml) will be tested against B. anthracis. Likewise, cyclic peptides that effectively kill other model bacteria will be contracted for testing against the corresponding select agent. In addition, cyclic peptides that exhibit antibiotic activity against several model species will be tested against a panel of medically relevant pathogens if they are indicated for development as broad-spectrum antibiotics or antibiotics against specific pathogens. In all cases testing will determine the MIC by broth dilution assays. Cyclic peptides that efficiently kill *B. anthracis* or other select agents, or that are effective against a wide spectrum of bacteria, will be transferred to government labs or the pharmaceutical industry for late stage development. To facilitate this transfer and development, the mechanism of action will be determined as described below.

Plasmid elimination activity: Because the tmRNA pathway is essential for plasmid maintenance in some species, it is possible that inhibitors of this pathway will act as plasmid elimination agents to kill bacteria that carry antibiotic resistance genes on extrachromosomal elements, or abrogate the pathogenicity of bacterial that carry virulence genes on a plasmid. The plasmid elimination activity will be tested in the model organisms *B. subtilis, C. crescentus*, and *E. coli*. The model bacterium bearing a plasmid, pUB110 for *B. subtilis*, pRK2 for *C. crescentus*, and F for *E. coli* will be incubated in culture with varying concentrations of purified cyclic peptide. The percentage of cells that have eliminated the plasmid after treatment with cyclic peptide will be determined by comparing the colony forming units (cfu) on selective medium to the cfu in the absence of selection. To control for cell killing by the cyclic peptide, assays will be duplicated without addition of cyclic peptide. The concentration of cyclic peptide that eliminates plasmid from 99.9% of the cells will be determined, if selected cyclic peptides act efficiently as plasmid elimination agents in these model organisms, the assays will be repeated in *B. anthracis* or the corresponding related pathogen to test for elimination of the native virulence plasmids or plasmid-borne antibiotic resistance genes.

Identification of molecular targets: Cyclic peptides that have antibacterial activity will be of interest irrespective of their molecular targets or mode of killing In addition, these experiments will confirm that the selection described above is working and guide future antibiotic development. The reaction that is targeted by each inhibitor in vivo will be identified using the EYFP-trpAt and EGFP-tag reporter strains. Inhibitors of tmRNA tagging should produce yellow fluorescence when incubated with the EYFP-trpAt strain, but no fluorescence when incubated with the EGFP-tag strain, whereas inhibitors of proteolysis of tagged proteins should produce fluorescence when incubated with either strain. Inhibition of the relevant reaction will then be confirmed using established in vitro assays with purified components. More specific assays will then be used to determine which molecular interactions are inhibited by the cyclic peptide.

The tagging activity of tmRNA will be assayed in a reconstituted in vitro translation system using poly(U) RNA as a template. This RNA has no stop codon, and is a substrate for tmRNA in vitro. Tagging is measured by incorporation of [$^{14}$C]-alanine into peptides, which can only occur through tmRNA tagging. An *E. coli* T7 coupled transcription/translation system (Promega) is used with the addition of tmRNA and poly(U). TCA is added to stop the reaction and precipitate peptides, which are collected on a glass fiber filter under vacuum. The incorporation of [$^{14}$C]-alanine is determined by scintillation counting. The inhibition of this reaction by purified cyclic peptides will be determined by including increasing amounts of cyclic peptide in the reaction. A non-inhibiting cyclic peptide will be used as a negative control. If tagging is inhibited, the steps that could be blocked are interaction of tmRNA with SmpB, and association of the tmRNA-SmpB complex with the ribosome. Because the *E. coli* reporter cells are viable during the screen, inhibitors of general translation factors such as alanyl-tRNA synthetase, EF-Tu, and the ribosome will not be isolated. These factors are inhibited by existing classes of antibiotics and are not targeted in this project. The effect of cyclic peptides on the binding of SmpB to tmRNA will be measured using filter-binding assays with purified SmpB and tmRNA generated from in vitro transcription. The $K_d$ for this interaction in the absence of inhibitor is 2 nM Inhibition of this interaction will be assessed by incubating excess cyclic peptide and tmRNA with 0.5-50 nM SmpB and evaluating the percentage of SmpB that is bound to tmRNA. If inhibition is observed, the $K_I$ will be determined to ensure that interaction with the peptide is specific and high affinity If the cyclic peptide does not alter the interaction of SmpB and tmRNA, it is likely that inhibition occurs at the step of association of tmRNA entry into the ribosome. However, in vitro assays for this association have not been established.

Inhibition of ClpXP proteolysis will be assayed in vitro using purified EGFP-tag as a substrate. Degradation of EGFP-tag by purified ClpXP is monitored by loss of fluorescence in a continuous spectroscopic assay (Levchenko et al. (2000) Science 289, p. 2354) Inhibitors of ClpXP degradation could block binding of the tagged substrate by SspB, interaction of SspB with ClpX, assembly of the ClpXP multi-subunit complex, substrate binding by ClpX, or inhibit the proteolytic active site of ClpP. Spectroscopic proteolysis assays will be performed using EGFP-tag, ClpXP, and purified cyclic peptide in the presence and absence of the proteolytic adaptor SspB. Assays will be repeated with varying concentrations of cyclic peptide inhibitor to determine if the inhibition is competitive or non-competitive. Competitive inhibition of ClpXP in the absence of SspB will indicate that the cyclic peptide is an active-site inhibitor of the protease. Non-competitive inhibition of proteolysis will suggest that the cyclic peptide inactivates the protease by another mechanism, such as preventing association of the ClpX and ClpP subunits. In this case, the association of ClpX and ClpP can be assayed by gel filtration Inhibition of proteolysis only in the presence of SspB will indicate that the cyclic peptide is interfering with the binding of SspB to the tagged protein, or with the binding of SspB to ClpX. Cross-linking and fluorescence anisotropy assays are available to test both of these interactions. These assays will elucidate the molecular target of cyclic peptide antibiotics, facilitating late-stage drug development.

Acquisition of resistance to antibiotic cyclic peptides: The rate at which bacteria can acquire mutations that confer resistance to an antibiotic is an important factor in the long-term efficacy of the drug. To ensure that resistance is not easily acquired to selected cyclic peptides, the rate of spontaneous mutations that lead to resistance will be determined by plating aliquots of cell cultures of known density on agar plates containing cyclic peptide at concentrations above the MBC. The appearance of colonies will indicate spontaneous mutants that are resistant to the cyclic peptide. The mutation rate will be calculated using the Luria-Delbruck method. For pharmacological use, this mutation rate should be $<10^{-9}$.

Discovery of Antimicrobial Cyclic Peptides that Inhibit the tmRNA Pathway.

Protein Purification: Lysis buffer contained 50 mM $NaPO_4$ (pH 8), 300 mM NaCl, and 10 mM Imidazole. Buffer A1 contained 50 mM Tris-HCl (pH 8), 10 mM MgCl2, 5 mM DTT, and 0.05 M KCl.

GFP containing the C-terminal E. coli ssrA tag was cloned into pTrc99 (Amersham Biosciences) resulting in an N-terminal His$_6$-tagged protein. E. coli ClpP was cloned into pQE70 (Qiagen) resulting in a C-terminal His$_6$-tagged protein. E. coli ClpX and SspB were cloned into pET28a (Novagen) resulting in N-terminal His$_6$-tagged proteins. GFP-ssrA, E. coli ClpX, ClpP, and SspB were purified in a similar manner described below. Proteins were purified from E. coli BL-21 pLysS cells (Novagen) grown in LB broth with the appropriate antibiotic to OD600=0.6, 1 mM IPTG was then added to induce overexpression, and cells were harvested after 3 hours. All purification steps were performed at 4° C. Cell pellets were resuspended in Lysis buffer at a concentration of 5 ml/g of cells. Cells were lysed by sonication (5.times.30 s), and the lysate was centrifuged at 15,000 rpm for 10 minutes. The resulting supernatant was applied to a column packed with Ni-NTA agarose (Qiagen) equilibrated with Lysis buffer. The column was then washed with 10 column volumes of Lysis buffer followed by 20 column volumes of 50 mM NaPO$_4$ (pH 8), 300 mM NaCl, and 20 mM Imidazole. The bound protein was eluted with 6 column volumes of 50 mM NaPO$_4$ (pH 8), 300 mM NaCl, and 250 mM Imidazole. ClpX was dialyzed against 50 mM Tris-HCl (pH 7.5), 300 mM NaCl, 2 mM DTT, and 10% glycerol. GFP-ssrA, ClpP, and SspB were purified further by anion exchange chromatography in a similar manner. The proteins were loaded onto HR 5/5 MonoQ column equilibrated with buffer A1, and eluted with a 0.05 to 1 M KCl gradient. Fractions containing protein were pooled and dialyzed against 50 mM Tris-HCl (pH 7.5), 100 mM NaCl, 2 mM DTT, and 10% glycerol for ClpP and SspB. Fractions containing GFP-ssrA were dialyzed against 50 mM Tris-HCl (pH 7.5) and 100 mM NaCl. Protein purity was estimated to be >95% by SDS-PAGE. Protein concentrations were determined (Bio-Rad) as per manufacturer's instructions. All proteins were stored at −80° C. in small aliquots.

Peptide Synthesis: Linear peptides were synthesized by the PSU Huck Institutes of the Life Sciences Macromolecular Core Facility (Hershey, Pa.). The cyclic peptides were prepared by head-to-tail chemical cyclization from a linear peptide as described (Horswill et al., 2004, Proc Natl Acad Sci USA 101, p. 15591).

Construction of SICLOPPS Library

Probe for tmRNA activity: A GFP-based probe that reports the degradation of tmRNA-tagged probes by ClpXP was constructed. The gene encoding GFP was PCR amplified from pEGFP-N2 (BD Biosciences Clontech) with primers that add the codons for the tmRNA peptide at the 3' end of the gene, and subsequently cloned into pTrc99 (Amersham Biosciences).

Screen for inhibitors of the tmRNA pathway: The 9-mer SICLOPPS library was transformed into E. coli SB75 cells containing the GFP-ssrA reporter construct. This SICLOPPS library/GFP-ssrA reporter culture was grown overnight in LB+amp(50 μg/ml)+chlor(20 μg/ml)+arabinose(0.0002%). The culture was then diluted 1:5 in fresh LB+amp+chlor+arabinose. IPTG was added to 1 mM and the culture was grown for 4 hours. At this point fluorescence activated cell sorting (FACS) was used to separate cells that contain an inhibitor from those that do not.

Clonal populations are obtained by spotting the cells with high fluorescence on agar plates, and cells from each colony are screened by epi-fluorescence microscopy for fluorescence intensity. SICLOPPS plasmids from clones that pass the microscopy screen were isolated and sequenced to identify the cyclic peptide that is produced in that clone.

ClpXP Proteolysis: PD buffer contained 25 mM HEPES-KOH (pH 7.6), 5 mM KCl, 5 mM MgCl$_2$, 0.032% NP-40, 5 mM ATP, and 10% glycerol. The ATP regenerating system consisted of 8 mM creatine phosphate and 0.16 mg/ml creatine kinase Inhibition experiments were performed using a Hitachi F-2000 Fluorescence Spectrophotometer. The rate of GFP-ssrA degradation was monitored at 30° C. for 5 minutes by the loss of fluorescence (excitation 488 nm; emission 507 nm). Competition experiments with increasing concentrations of peptide were performed using GFP-ssrA (0.2 μM), ClpX$_6$ (0.3 μM), ClpP14 (0.8 μM), and SspB2 (0.3 μM) in PD buffer plus 200 mM KCl and ATP regenerating system. Curve fitting for the competitive inhibition assays were performed using the Scientist program (MicroMath Scientific Software, Inc.).

Antibacterial activity: The peptides recovered from the selection were tested for antibacterial activity by incubating a 1:1,000 diluted saturated culture with the peptide overnight at room temperature. For each peptide a series of concentrations were tested. The mix was then plated, and the colonies were counted after a period incubation at 30° for C. crescentus or 37° C. for B. subtilis. For C. crescentus, PYE liquid media were incubated overnight at 30° C. at 250 rpm, and PYE plates were incubated for 3 days at 30° C. For B. subtilis, LB liquid media and plates were incubated overnight at 37° C. The Minimal Bactericidal Concentration (MBC) reported is the peptide concentration at which there were fewer than 0.1% colonies compared to wild type.

Figure 1B:
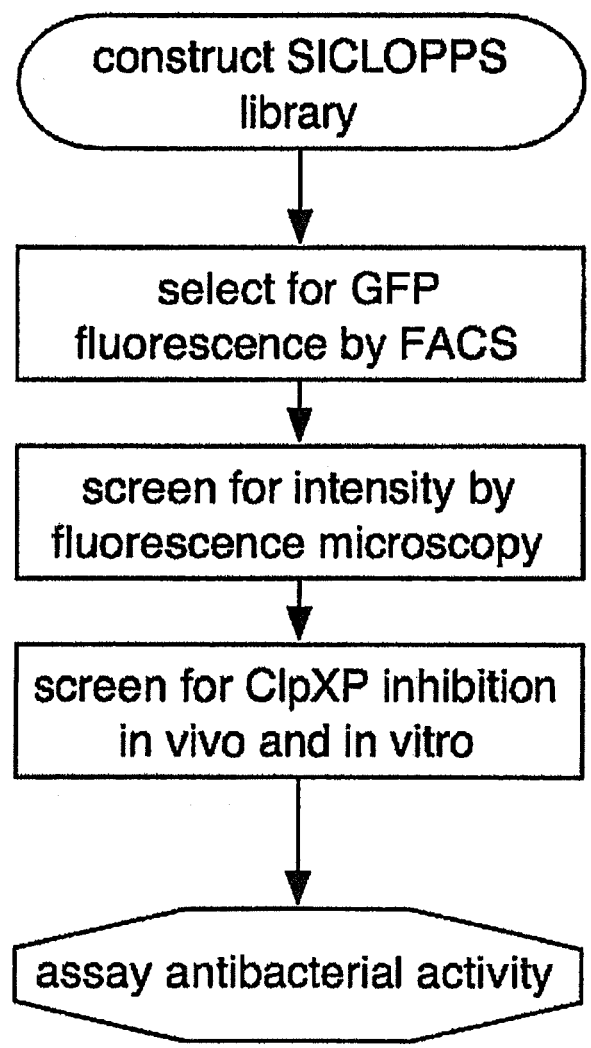
FIG. 1B is a schematic illustration showing one aspect of the experimental design.

Selection of ClpXP inhibitors in vivo: To identify inhibitors of ClpXP degradation of tmRNA-tagged proteins, a library of plasmids encoding 9 amino acid circular peptides was generated using by randomizing 5 out of the 9 codons in the SICLOPPS peptide coding sequence (FIG. 1B). The wild-type codons were replaced with NNS, where N represents any base and S represents G or C. This redundant codon can encode any of the 20 amino acids, but reduces the probability of a stop codon and results in a more even distribution of encoded amino acids. The resulting library theoretically encodes 3.2.times.10$^6$ different cyclic peptides. Expression of the SICLOPPS construct was placed under the control of the arabinose promoter such that addition of arabinose activated expression of the SICLOPPS protein. The subsequent spontaneous cyclization to produce a 9 amino acid cyclic peptide was confirmed by purification of cyclic peptides by butanol extraction and reversed-phase chromatography followed by mass spectrometric analysis.

A reporter for proteolysis of tmRNA-tagged proteins was engineered by encoding the tmRNA peptide at the 3' end of the egfp gene, such that expression of this gene produces a variant of GFP that contains the tmRNA peptide (GFP-tag). When GFP-tag was produced in wild-type E. coli, the cells showed little fluorescence and GFP-tag could not be detected by Western blotting, presumably because the protein was recognized as a tmRNA-tagged protein by SspB and rapidly degraded by ClpXP. In an E. coli strain deleted for clpX, GFP-tag accumulated to high levels and resulted in cells that were highly fluorescent, indicating that ClpXP activity is required for efficient degradation of GFP-tag. Likewise, wild-type E. coli were highly fluorescent when producing a variant of GFP-tag lacking the ClpXP epitope at the C terminus (GFP-tagDD). Thus normal ClpXP activity is sufficient to degrade the GFP-tag that is produced in vivo, resulting in nonfluorescent cells, but cells containing an inhibitor of ClpXP are expected to be fluorescent.

To isolate cyclic peptides that inhibit degradation of tmRNA-tagged proteins, the SICLOPPS plasmid library was transformed into E. coli and expression of both cyclic peptides and gfp-tag was induced. Fluorescent cells were separated from the culture containing predominantly non-fluorescent cells using Fluorescence Activated Cell Sorting (FACS). From $1.6 \times 10^6$ cells sorted by FACS, 171 (approximately 0.1% of the population) were selected as having fluorescence over the background level. To eliminate clones that resulted from sorting errors or stochastic or spurious accumulation of GFP, a secondary screen for fluorescence was employed. Cells from each colony were cultured in liquid medium under conditions that induced production of the cyclic peptide and GFP-tag, and observed using epifluorescence microscopy. In 43 clones fluorescence intensity was within 50% of the ΔclpX strain, and in 6 clones the intensity was indistinguishable from the ΔclpX strain (FIGS. 2A-2C). In addition, cells containing these plasmids had a filamentous morphology similar to the ΔclpX strain. These 6 clones were chosen for further characterization. To ensure that the high fluorescence intensity was due to the cyclic peptide produced from the SICLOPPS plasmid and not from a chromosomal mutation, plasmid DNA was prepared from each clone and transformed into a naive reporter strain. In all cases, high fluorescence intensity segregated with the plasmid. These plasmids were sequenced to identify the cyclic peptides that are encoded, and the peptide sequences are shown in Table 4.

Figure 3:
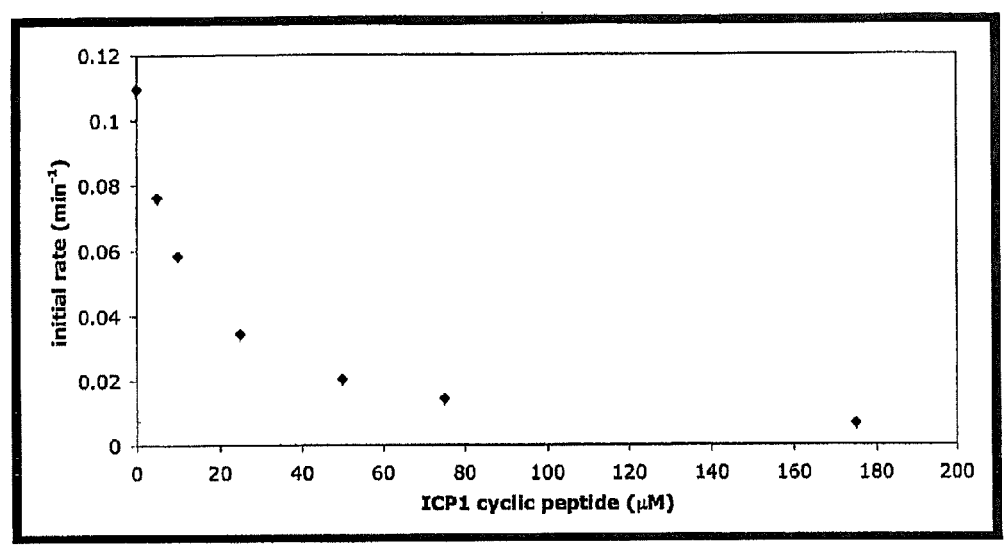
FIG. 3 is a graph showing selected cyclic peptides inhibit degradation of GFP-tag by ClpXP in vitro. Cyclic peptides were chemically synthesized and added to reactions containing ClpXP, SspB, GFP-tag, and ATP, and proteolysis of GFP-tag was monitored by loss of fluorescence. The initial rate of the reaction is plotted versus the concentration of the ICP1 cyclic peptide.

Characterization of ClpXP inhibitors in vitro: Two of the selected cyclic peptides were synthesized in vitro to examine their effects on enzymatic assays. Peptides with the sequence SGWRVQGPL (SEQ ID NO: 1) and SGSKGVLPL (SEQ ID NO: 2) were chemically synthesized in the linear form, circularized, and purified by HPLC. The effects of these peptides on the activity of purified ClpXP were determined in vitro using a continuous fluorimetric assay. GFP-tag, SspB, ClpX and ClpP were each purified from over-expressing strains of E. coli, and degradation of GFP-tag was monitored by loss of fluorescence. In reactions containing all components, GFP-tag was degraded with kinetic parameters kcat=1.79±0.08 min–1, $K_M$=0.74±0.04, similar to the previously published values of 1.44 min$^{-1}$ and 0.96 µM. No measurable degradation was observed when ClpX or ClpP were omitted from the reaction, indicating that degradation in vitro is due to ClpXP activity. Likewise, no degradation was observed for wild-type GFP with no tmRNA tag, or for GFP-tagDD, confirming that susceptibility to ClpXP depends on the tmRNA tag. Inclusion of either purified cyclic peptide resulted in competitive inhibition of ClpXP activity, with $K_I$ values 21-25 µM (FIG. 3). For both cyclic peptides, inhibition of ClpXP was reversible, as no inhibition was observed when ClpXP was incubated with peptide at concentrations above the $K_I$, and dialyzed to remove unbound peptide before addition of enzyme to the reaction. The linear versions of SGSKGVLPL (SEQ ID NO: 2) and SGWRVQGPL (SEQ ID NO: 1) had $K_I$ values >1 mM (Table 4), so the cyclic architecture is likely to be important for inhibition. A cyclic peptide of arbitrary sequence showed no detectable inhibition in vitro, demonstrating that both the cyclic architecture and the amino acid sequence of the selected cyclic peptides are important for efficient ClpXP inhibition.

A priori, there are several steps in the degradation pathway that could be inhibited by the selected cyclic peptides: binding of the substrate-SspB complex to ClpXP, ATPase activity of ClpX, and hydrolysis of the peptide bond by ClpP. Molecules that block the binding of substrate to SspB should not be inhibitors of proteolysis by ClpXP, because ClpXP will degrade tmRNA-tagged substrates in the absence of SspB. To determine if the inhibitors act through SspB, the kinetic assays were repeated in the absence of this proteolytic adaptor. ClpXP degraded GFP-tag in the absence of SspB with slightly decreased efficiency, in accord with previous studies. The cyclic SGSKGVLPL (SEQ ID NO: 2) peptide inhibited degradation of GFP-tag by ClpXP in the absence of SspB, suggesting that it acts directly on ClpXP. The peptide did not inhibit ClpXP in the absence of SspB in the concentration range tested, indicating a $K_I$ value at least 10-fold higher. These data suggest that cyclic SGWRVQGPL (SEQ ID NO: 1) blocks binding of the substrate-SspB complex to ClpX. Gel filtration assays to monitor the interaction of GFP-tag with SspB showed that neither cyclic peptide affected SspB binding to substrate.

The differing effects of SspB on inhibition indicate that inhibitors for two different steps in the ClpXP degradation pathway were obtained from the genetic screen. To confirm the different specificities of these two inhibitors, the effects on ClpXP degradation of a substrate unrelated to tmRNA tagged proteins was assayed. Because ClpXP can recognize at least 5 different protein sequences as substrate determinants, it has been proposed that there are several substrate binding sites on the protease. Inhibitors that block one site of interaction are expected to affect degradation of only the substrates that bind at that site. Conversely, inhibitors that block catalysis or obstruct a binding site required by all substrates should affect degradation of any ClpXP substrate. The degradation of λO protein, a substrate of ClpXP recognized by sequences at both the N and C terminus that does not interact with SspB, was assayed in the presence of the selected cyclic peptide inhibitors. The cyclic SGSKGVLPL (SEQ ID NO: 2) peptide inhibited degradation of λO protein at concentrations near the $K_I$ value for degradation of GFP-tag, indicating that it is an inhibitor of the degradation of both proteins. The cyclic SGWRVQGPL (SEQ ID NO: 1) peptide had no effect on degradation of λO protein, even at concentrations 10-fold above the $K_I$ value for degradation of GFP-tag, indicating that this peptide is a specific inhibitor of the degradation of proteins with the tmRNA tag. These data are consistent with cyclic SGWRVQGPL (SEQ ID NO: 1) interfering with the binding of the SspB-substrate complex to ClpXP.

Therefore, the genetic selection identified inhibitors of the degradation of tmRNA substrates that act at two distinct steps in the proteolytic mechanism. One peptide inhibitor of SspB-ClpXP interaction has already been described. The XB peptide, comprising the 11 C terminal amino acids from SspB known to bind to ClpX, competes with SspB for binding to ClpX and inhibits the degradation of GFP-tag in the presence of SspB. Using the linear XB peptide as a positive control in the assays described above, it was confirmed that this peptide is a competitive inhibitor of ClpXP degradation of GFP-tag in the presence of SspB. The XB peptide inhibited degradation of GFP-tag by ClpXP in the presence of SspB with a $K_I$=6.4±3.6 µM, similar to the previously published value, and had no effect on the reaction in the absence of SspB. Linear XB peptide also did not inhibit the degradation of λO protein. These results are similar to those obtained for the cyclic SGWRVQGPL (SEQ ID NO: 1) peptide, suggesting that this cyclic peptide also inhibits the binding of SspB to ClpX. However, there is very little sequence similarity between these peptides.

To test if a cyclic architecture would increase the efficiency of inhibition by XB, the peptide was cyclized in vitro and cyclic XB was tested in the ClpXP activity assays. Cyclic XB inhibited ClpXP proteolysis of GFP-tag in the presence of SspB with a $K_I$=8.1 µM, 7-fold lower than the linear XB peptide and 2-3 fold lower than the selected cyclic peptide inhibitors. Surprisingly, the cyclic XB peptide inhibited degradation of GFP-tag even in the absence of SspB. This result implies that cyclic XB has a different or additional mode of inhibition to the linear form of the peptide.

Antibacterial activity of cyclic peptide inhibitors: Because ClpXP is essential in *C. crescentus*, we examined whether the inhibitory peptides have any effect when added exogenously to growing cultures. The selected cyclic peptides killed *C. crescentus* with a minimum inhibitory concentration (MIC) of 62.5 µM, as did the linear XB peptide. The cyclic XB peptide was more effective, with an MIC less than 32 µM, but an arbitrary cyclic peptide (con62) had no effect on bacterial growth. ClpXP is not essential in *Bacillus subtilis*, but mutants lacking ClpXP activity have growth and sporulation defects. The selected cyclic peptides also kill *B. subtilis* when added to growing cultures, with an MBC of 250-500 µM. No killing of *E. coli* or the related γ-proteobacteria *Shigella flexneri* and *Vibrio cholera* was observed. It remains to be determined if the selected cyclic peptides are effective against pathogenic bacterial that require the tmRNA-ClpXP pathway.

Conclusions: Using a rapid selection strategy and SICLOPPS technology, efficient inhibitors of the degradation of tmRNA-tagged proteins were isolated that act at two distinct steps in the pathway. In principle, this screening technique could be employed to identify cyclic peptide inhibitors for any pathway with a fluorescent reporter that can be expressed in *E. coli*. Despite the anticipated problems of transporting a cyclic peptide across the membrane of Gram-negative bacteria, two of the selected cyclic peptides and the cyclic XB peptide have bactericidal activity. Although the MIC values are not as low as many antibiotics, several optimization steps are available to improve the bio-activity of these compounds. Because only 5 residues in the cyclic peptide were randomized in this trial, a relatively small amount of sequence space was sampled. Nevertheless, each of the selected peptides is a more efficient inhibitor than the rationally designed XB peptide. Randomizing 8 residues in the 9-mer SICLOPPS peptides would increase the pool of available sequences over 8000-fold. In addition, the 11-mer cyclic XB peptide is a more efficient inhibitor of ClpXP and has a lower MIC, so better peptide sequences could be accessed by increasing the chain length. Further improvements to the efficacy of these inhibitors could be made through modification or derivatization of the peptide, or the use of non-standard amino acids. The mechanism by which the cyclic peptides kill *C. crescentus* has not been demonstrated. Because there is little sequence similarity in the selected cyclic peptides, and an arbitrary cyclic peptide that does not inhibit ClpXP has no effect on bacterial growth, it is likely that the peptides enter the cytoplasm and act through ClpXP. However, it is formally possible that these peptides kill the cells through an unrelated mechanism.

TABLE 4

Characterization of inhibitors of the tmRNA pathway

| Peptide | Linkage | Sequence | $K_I$ value +SspB (µM) | $K_I$ value No SspB (µM) | MIC (µM) |
|---|---|---|---|---|---|
| ICP1 | cyclic | [SGSKGVLPL] (SEQ ID NO: 2) | 25 ± 6 | 28 ± 2 | 62.2 |
| ICP2 | cyclic | [SGWRVQGPL] (SEQ ID NO: 1) | 21 ± 5 | >1000 | 62.2 |

TABLE 4-continued

Characterization of inhibitors of the tmRNA pathway

| Peptide | Linkage | Sequence | $K_I$ value +SspB (µM) | $K_I$ value No SspB (µM) | MIC (µM) |
|---|---|---|---|---|---|
| linICP1 | linear | SGSKGVLPL (SEQ ID NO: 2) | >1500 | >1500 | >250 |
| linICP2 | linear | SGWRVQGPL (SEQ ID NO: 1) | >1500 | >1500 | >250 |
| linXB | linear | CRGGRPALRVVK (SEQ ID NO: 3) | 64 ± 9 | >1000 | 62.2 |
| cycXB | cyclic | [CRGGRPALRVVK] (SEQ ID NO: 3) | 8 ± 1 | 6 ± 4 | 31.3 |
| Con62 | cyclic | [SGWPYKWM] (SEQ ID NO: 4) | >1000 | >1000 | >250 |

A SICLOPPS library was constructed in which the cyclic peptide contains three constant amino acids, SGW, followed by five random amino acids encoded by NNS codons. This library was introduced into cells containing the GFP-tag reporter, and the expression of the reporter and cyclic peptide were induced. Approximately 690,000 cells were sorted by FACS and the brightest 50 were isolated. These 50 clones were grown individually in fresh medium, the expression of reporter and cyclic peptide was induced, and the culture was observed by epifluorescence microscopy. Two clones produced cultures in which nearly 100% of the cells were highly fluorescent. In both cases, the average fluorescent intensity of the cells was more than twice the average from cultures expressing ICP1 or ICP2. Sequencing of the DNA from the randomized region of the SICLOPPS plasmids indicated that the encoded peptides are cyclic SGWHRRGM (SEQ ID NO: 5) and cyclic SGWYGRRH (SEQ ID NO: 6). These results indicate that both 9-mer and 8-mer cyclic peptides can inhibit the degradation of tmRNA-tagged proteins, and suggest that the sequence (G/H)RR(G/H) result in strong inhibition.

Example 2

Fate of tmRNA-Tagged Proteins a Pathway to New Antibiotics

SsrA, or tmRNA, is a small RNA that adds a short peptide tag to the C terminus of nascent polypeptides on stalled ribosomes. This tagging pathway is required for development and virulence in many species, and in *Caulobacter crescentus* it is required for normal cell cycle progression. In both *C. crescentus* and *E. coli*, most SsrA tagged proteins are rapidly degraded. Their fate depends on interactions with at least 4 proteases and 2 proteolytic adaptor proteins. In *E. coli*, most tagged proteins targeted for degradation bind to the proteolytic adaptor protein SspB, which delivers the substrate to the ClpXP protease. ClpXP is essential in *C. crescentus*, and we have identified a protein, SmpD, that performs the same functions as SspB. SmpD binds to the SsrA-encoded peptide tag in vitro, and in a strain deleted for smpD the half-life of tagged proteins is increased 3.5-fold in vivo. mRNA profiling and Western blot experiments demonstrate that SmpD is cell-cycle regulated at the mRNA and protein level, with peak expression during the swarmer-to-stalked cell transition, coincident with the peak in SsrA levels. These results are consistent with a role for SmpD in facilitating the degradation of SsrA-tagged proteins. However, a strain deleted for smpD does not have the ssrA phenotype. Therefore, either degradation of tagged proteins is not important for the ssrA phenotype, or there are pathways redundant to SmpD. To test for the importance of degradation of SsrA-tagged proteins, we performed a genetic screen for small-molecule inhibitors of the proteolytic pathway. A library of cyclic peptides was produced in E. coli using SICLOPPS technology (split intein-mediated circular ligation of peptides and proteins), and those that inhibited the degradation of a GFP-SsrA reporter were isolated by FACS. Assays in vitro demonstrated that these cyclic peptides are bona fide inhibitors of SspB-ClpXP-mediated degradation of tagged proteins (KI=21-26 µM). These inhibitors are specific for the degradation of tagged proteins because no inhibition was observed in the absence of SspB. Linear versions of the cyclic peptides, and cyclic peptides of unrelated sequence, did not inhibit SspB-ClpXP. Addition of the cyclic peptide inhibitors to cultures of C. crescentus killed the cells with minimum bactericidal concentrations of 60 µM.

Conclusions: Half-life of SsrA-tagged substrates increase in AsmpD. SmpD directly interacts with the *Caulobacter* SsrA-tag in vitro. Cyclic peptide inhibitors of the SsrA pathway by FACS and in vivo methods were identified. In vitro inhibition of ClpXP by cyclic peptides. Cyclic peptide inhibitors have antimicrobial activity.

The basis for this lethality is under investigation.

Example 3

Antibacterial Cyclic Peptides that Inhibit the ClpXP Protease

To determine if inhibitors of ClpXP would have antibacterial activity against species that require this protease, a bacterial strain in which ClpXP is not essential was used to screen for cyclic peptides that block degradation of tmRNA-tagged proteins. Synthetic versions of these inhibitors were then tested for bactericidal activity against *Caulobacter crescentus*, a gram-negative bacterium in which clpX and clpP are essential.

Materials and Methods

Plasmids and bacterial strains: A GFP-based reporter for the proteolysis of tmRNA tagged proteins was constructed by amplifying the egfp gene from pEGFP-N2 (BD Biosciences Clontech) using PCR with primers that add the codons for the tmRNA tag (AANDENYALAA; SEQ ID NO: 7) at the 3' end of the gene before the stop codon, and cloning the product into pTrc99a. A similar strategy was employed for the control reporters containing egfp with no tag and egfp with the DD tag (AANDENYALDD; SEQ ID NO:8). For fluorescence assays, plasmids bearing a GFP-based reporter were mobilized into E. coli strain BW7786 (Khlebnikov et al. 2001; Microbiology 147: 3241-3247). The ΔclpXstrain was constructed from BW7786 using the Wanner method (Datsenko and Wanner 2000, Proc. Natl. Acad. Sci. USA 97: 6640-6645).

For over-production of GFP-tag, GFP, and GFP-tagDD, the genes were excised from pTrc99a, ligated into pQE8 (Qiagen, Valencia, Calif.) to produce an N-terminal His6-fusion under control of the T7 promoter, and mobilized into E. coli BL21(DE3) (Novagen, San Diego, Calif.). E. coli clpP was cloned into pQE70 (Qiagen) resulting in a C-terminally His6-tagged protein. E. coli ClpX, sspB and the gene encoding λ O were cloned into pET28a (Novagen) to produce N-terminally His6-tagged proteins. All constructs were transformed into E. coli BL21(DE3). Unless otherwise noted, E. coli strains were grown at 37° C. in LB broth, with the addition of 100 µg/ml ampicillin, 30 µg/ml chloramphenicol, or 30 µg/mlkanamycin where appropriate. C. crescentus strain CB 15N (Evinger and Agabian 1977; J. Bacteriol. 132: 294-301) was grown in PYE medium (Ely 1991; Methods in Enzymology 204: 372-384).

SICLOPPS libraries were constructed as previously described (Abel-Santos et al. 2003. Methods Mol Biol 205: 281-294). For the $SGWX_5$ library the initial PCR reaction combined degenerate oligonucleotide SGW+5 (5'-ggaattcgccaatggggcgatcgcccacaattccggctggnnsnnsnnsnnsnnstgcttaagttttgg-c-3'; SEQ ID NO: 9) and CBDRev (ggaattcaagctttcattgaagctgc-cacaagg; SEQ ID NO: 10). For the second PCR reaction CBDRev was combined with a forward primer named zipper (ggaattcgccaatggggcgatcgcc; SEQ ID NO: 11). Production of cyclic peptides from the $SGX_5PL$ (SEQ ID NO:13) library in E. coli was confirmed by butanol extraction and reversed-phase chromatography followed by mass spectrometric analysis of the purified cyclic peptides as described (Scott et al. 2001, Chem Biol 8: 801-815).

Proteins and peptides: Histidine-tagged versions of ClpP, ClpX, SspB, GFP, GFP-tag, GFP-tagDD and λ O protein were purified from over-producing strains by metal-chelate chromatography followed by ion exchange chromatography, gel filtration, or both. In all cases, cells were grown at 30° C. in LB broth with the appropriate antibiotics to $OD_{600}$=0.6, 1 mM IPTG was added to induce protein production for 3.5 h, and cells were harvested by centrifugation. Cell pellets were resuspended in Wash buffer (50 mM $NaH_2PO_4$ (pH 8.0), 300 mM NaCl, 20 mM imidazole), lysed by sonication, and cleared by centrifugation at 26,000.times.g for 15 min. The cleared lysate was added to 0.1% v/v Ni-NTA resin (Qiagen) for 1 h, loaded into a column, and washed with 100 bed volumes of Wash buffer. Bound protein was eluted with 5 bed volumes of Wash buffer containing 500 mM imidazole, and fractions containing purified protein were identified by SDS-PAGE.

Fractions containing purified ClpX were combined, applied to a Superose 6 (GE Healthcare) gel filtration column equilibrated in buffer containing 50 mM Tris-HCl (pH 7.5), 300 mM NaCl, 2 mM DTT, and 10% glycerol, and fractions containing purified ClpX protein were identified by SDS-PAGE.

For purification of ClpP and λ O protein, fractions from metal-chelate chromatography were combined and dialyzed against buffer A1 (50 mM Tris-HCl (pH 8), 10 mM $MgCl_2$, 5 mM DTT, 10 mM KCl) and applied to a MonoQ HR5/5 column (GE Healthcare, Piscataway, N.J.). The column was washed in buffer A1 and bound protein was eluted with a linear gradient from 10 to 1000 mM KCl. Fractions containing purified protein were combined and dialyzed against buffer A2 (50 mM Tris-HCl (pH 7.5), 100 mM NaCl, 2 mM DTT, and 10% glycerol).

GFP, GFP-tag, and GFP-tagDD were purified as described for ClpP, except that fractions from the MonoQ column containing purified protein were applied to a Superdex 75 (GE Healthcare) gel filtration column equilibrated in buffer A2, and fractions containing the GFP variant were combined.

SspB was purified as described for ClpP, except that buffer A3 (50 mM MES (pH 6), 10 mM MgCl2, 1 mM DTT, 100 mM KCl) was used in place of buffer A1. For all proteins, concentrations were determined by UV absorbance at 280 nm.

Linear peptides were synthesized by the PSU Huck Institutes of the Life Sciences Macromolecular Core Facility (Hershey, Pa.). Linear peptides were cyclized by incubating peptide with excess 1-ethyl-3-(3'-dimethylaminopropyl)carbodiimeide (EDC) and 1-hydroxy-7-azabenzotriazole (HOAt) in 50 mL DMF. After 24 hours of incubation, an aliquot of each reaction was analyzed by RP-HPLC to confirm cyclization. Successful reactions were assumed based on increased retention time of peptide relative to the retention time of linear starting products. Reactions were evaporated and peptides partially purified by precipitation with diethyl ether. Final purification of cyclic peptides was accomplished by RP-HPLC. Mass was confirmed by use of electrospray-ionization mass spectrometry.

Screen for inhibitors of the tmRNA pathway: *E. coli* BW7786 cells containing the GFP-tag reporter and the SICLOPPS library were grown in LB broth with 30 μg/ml chloramphenicol, 100 μg/ml ampicillin, and 0.0002% arabinose at 37° C. to $OD_{600}$=0.3. IPTG was added to a final concentration of 1 mM, and the culture was grown for 3 hours. Cells were sorted by fluorescence activated cell sorting (FACS) using a Beckman Coulter Elite cell sorter with Autoclone to isolate cells with GFP fluorescence, and selected cells were deposited on agar plates for clonal growth. Cells from each colony were grown in liquid culture as described above and examined by epifluorescence microscopy. The fluorescence intensity and the number of cells with fluorescence above background were scored using ImagePro software (MediaCybernetics). SICLOPPS plasmid DNA was prepared from selected clones and the region encoding the cyclic peptide was sequenced. Peptide sequences were obtained from conceptual translation of the DNA sequences.

In vitro proteolysis assays: Proteolysis of GFP-tag was performed using a continuous fluorescence assay essentially as previously described (Levchenko et al. 2000, Science 289: 2354-2356). Briefly, loss of GFP fluorescence was monitored at 507 nm after excitation at 395 nm at 30° C. using a Hitachi F-2000 Fluorescence Spectrophotometer in buffer R (25 mM HEPES-KOH (pH 7.6), 5 mM MgCl2, 50 mM KCl, 0.032% NP-40, 10% glycerol, and an ATP regeneration system containing 4 mM ATP (pH 7), 16 mM creatine phosphate and 0.32 mg/ml creatine kinase). Typically, reactions contained 0.1 μM $ClpX_6$, 0.3 μM $ClpP_{14}$, and equimolar concentrations (0.2 μM-2.0 μM) GFP-tag and SspB. Degradation of GFP-tag protein was confirmed by SDS-PAGE assays. To examine inhibition of GFP-tag proteolysis, peptides were incubated with ClpXP in reaction buffer for 5 min prior to the addition of GFP-tag. Plots of fluorescence versus time were fit with a single exponential function to determine the initial rate of proteolysis. Kinetic parameters were estimated using Eadie-Hofstee plots. Curve fitting for competitive inhibitors was performed using the Scientist program (MicroMath Scientific Software, Inc.).

Peptidase activity against IXP1 was assayed by incubating 200 μM IXP1 with 0.1 μM $ClpX_6$, 0.3 μM $ClpP_{14}$ and the ATP regeneration system in buffer R at 37° C. Sample were taken after 0, 5, and 60 min, and separated by reverse-phase HPLC using a Varian Microsorb-MV C18 column developed in a gradient from 0.1% trifluoroacetic acid in water to 0.1% trifluoroacetic acid in acetonitrile. UV absorbance at 280 nm was monitored and the peak corresponding to the IXP1 cyclic peptide was determined by comparison to reactions containing only cyclic IXP1 or linear IXP1. The loss of cyclic IXP1 was determined by integrating the area under the cyclic IXP1 peak.

Proteolysis of λ O protein was assayed by incubating 1 μM λ O with 0.1 μM $ClpX_6$, 0.3 μM $ClpP_{14}$ in buffer Rat 30° C. At various times the reaction was sampled, the reaction was terminated by boiling in SDS-PAGE loading buffer, and analyzed using SDS-polyacrylamide gels stained with Coomassie blue. The intensity of the band corresponding to intact λO protein was measured using ImageQuant software (Molecular Dynamics), and plots of the intensity versus time were fit with single exponential functions to determine the half-life of λ protein.

ATPase and peptidase assays: ClpX ATPase activity was measured by monitoring the increase in phosphate using a ternary hetero polyacid assay (Chen et al. 2003, Tsinghua Science and Technology 8: 422-427). 1 μM ClpX was incubated with or without 6 μM GFP-tag and varying concentrations of IXP1 in buffer P (4 mM ATP, 50 mM tris-HCl (pH 7.5), 100 mM NaCl, 100 mM KCl, 10 mM $MgCl_2$, 2 mM DTT, and 10% glycerol) at 37° C. At each time point 10 μl was removed from the reaction, added to 265 μl 0.88 M nitric acid for 2 min, and 225 μl color developing solution (44.4 mM bismuth nitrate, 31.1 mM ammonium molybdate, 0.11% ascorbic acid) was added and the absorbance at 700 nm was determined. The rate of ATP hydrolysis was determined from plots of phosphate accumulation versus time.

ClpP peptidase activity was measured using the fluorogenic peptide Suc-Leu-Tyr-AMC. 0.1 μM ClpP was incubated with 0.5-1.0 mM Suc-Leu-Tyr-AMC and varying concentrations of IXP1 in buffer P at 37° C. and monitoring the fluorescence of AMC (excitation at 353 nm, emission at 442 nm).

Antibacterial activity assays: To measure the effects of peptides on bacterial growth, cultures of *C. crescentus* were diluted to $OD_{660}$=0.001, peptide was added at various concentrations, the cultures were incubated at 30° C. for 14 h, and the MIC was determined as the lowest concentration of peptide that prevented growth. To determine the MBC, each culture was diluted 1:100 in PYE and 10 μl of the diluted culture was spread onto PYE agar plates, incubated at 30° C. overnight, and the number of colonies on each plate was counted. The MBC was assigned as the concentration of peptide that reduced the number of colonies by 99.9% compared to cultures with no inhibitor.

Results

Figure 4A:
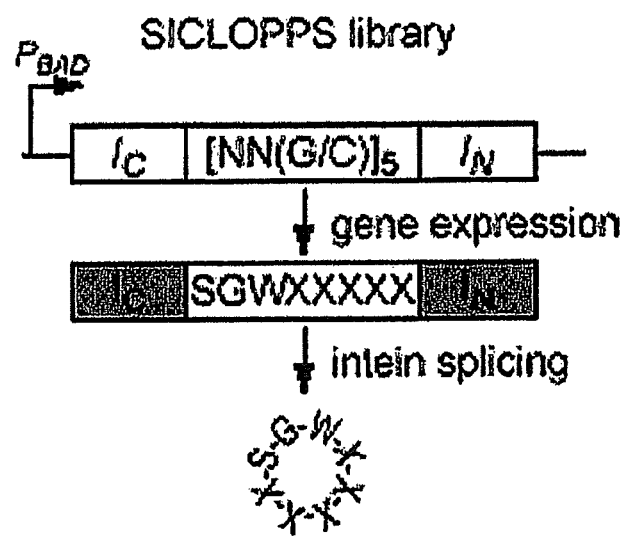
FIGS. 4A-4C show an illustrative method of selecting for cyclic peptide inhibitors of ClpXP.
Figure 4B:
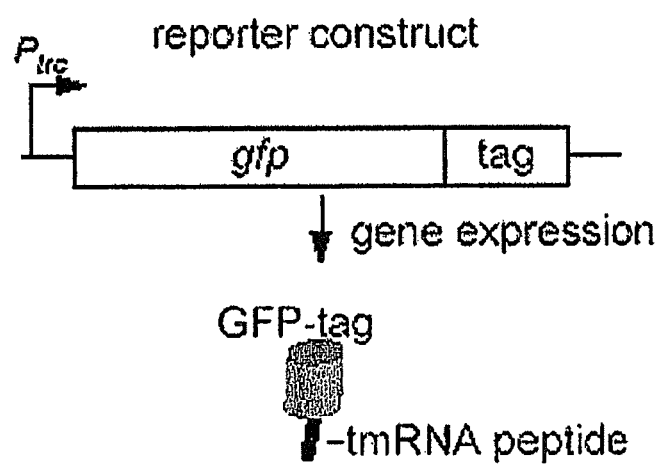
Figure 4C:
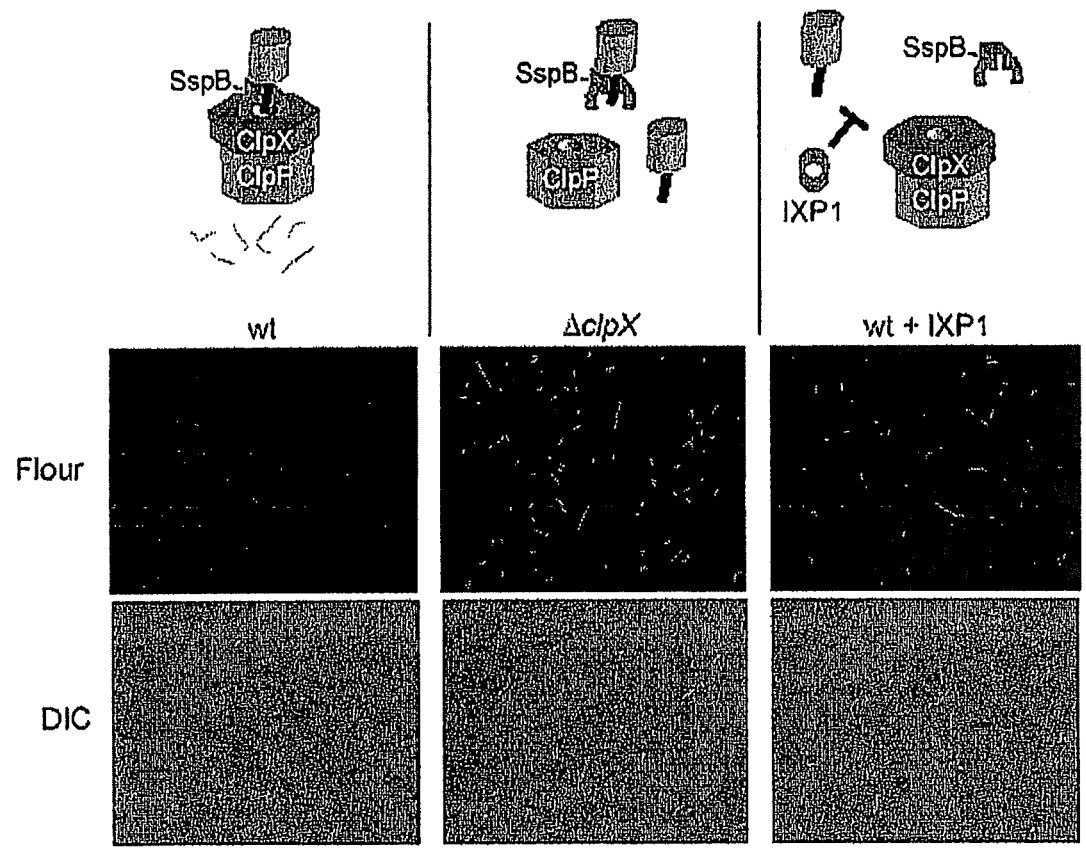

Screen for cyclic peptide inhibitors of ClpXP: To identify inhibitors of proteolysis of tmRNA-tagged proteins, a reporter was engineered by encoding the tmRNA peptide tag at the 3' end of the egfp gene, such that expression of this gene produces a variant of GFP containing the tmRNA peptide tag (GFP-tag) (FIG. 4B). When GFP-tag was produced in wild-type *E. coli*, the cells showed little fluorescence (FIG. 4C), presumably because the protein was recognized as a tmRNA-tagged protein and rapidly degraded by ClpXP. Degradation required both the tmRNA peptide tag and ClpX. When a variant of GFP with no tag or with a tag lacking the ClpXP recognition sequence at the C terminus (GFP-tagDD) was produced, the *E. coli* were highly fluorescent. Likewise, in an *E. coli* strain deleted for clpX, production of GFP-tag resulted in cells that were highly fluorescent (FIG. 4C). These results suggested that cells producing GFP-tag would be fluorescent if an inhibitor of ClpXP was present.

A library of SICLOPPS plasmids was constructed that encodes the sequence SGW followed by five NN(G/C)

codons. This SGWX$_5$ (SEQ ID NO: 12) library theoretically produces 3.2.times.10$^6$ different cyclic peptides. The SGW sequence allows efficient circular ligation, and the redundant codons can encode any of the 20 amino acids (Abel-Santos et al. 2003, Methods Mol Biol 205: 281-294). The use of NN(G/C) instead of fully redundant codons reduces the probability of a stop codon and results in a more even distribution of encoded amino acids.

To isolate cyclic peptides that inhibit proteolysis of tmRNA-tagged proteins, the SGWX$_5$ (SEQ ID NO: 12) SICLOPPS library was expressed in *E. coli* containing GFP-tag, and fluorescent cells were selected from a population of .about.10$^6$ using FACS. Most cells producing a cyclic peptide had little fluorescence, indicating that most cyclic peptides do not inhibit ClpXP. Approximately 0.014% of the population had fluorescence over the background level, and 96 of these cells were isolated for clonal growth and characterization. To eliminate any clones that resulted from sorting errors or spurious accumulation of GFP, cells from each colony were cultured and examined by epifluorescence microscopy. All selected clones produced some fluorescent cells (cells with fluorescence intensity at least 0.5-fold the level observed in ΔclpX cells producing GFP-tag), and two clones, containing the peptides IXP1 and IXP2, produced cells with fluorescence indistinguishable from the ΔclpX strain (FIG. 4C and Table 5).

To determine if other libraries of cyclic peptides also contained inhibitors of GFP-tag degradation, a SICLOPPS library of 9-mer peptides with the sequence SGX$_5$PL (SEQ ID NO: 13) was engineered and screened in the same manner as the SGWX$_5$ (SEQ ID NO: 12) library. Three clones (IXP3, IXP4, and IXP5) producing GFP fluorescence of similar intensity to the ΔclpX strain were isolated (Table 5).

TABLE 5

Cyclic peptides identified from in vivo screen.

| library | name | sequence | % fluorescent cells$^a$ |
|---|---|---|---|
| SGWX$_5$ library (SEQ ID NO: 12) | IXP1 | SGWYGRRH (SEQ ID NO: 6) | >80 |
| | IXP2 | SGWHRRGM (SEQ ID NO: 5) | 30-40 |
| | Con62 | SGWPYKWM (SEQ ID NO: 4) | 0 |
| SGX$_5$PL library (SEQ ID NO: 13) | IXP3 | SGSKGVLPL (SEQ ID NO: 2) | 70-80 |
| | IXP4 | SGWRVQGPL (SEQ ID NO: 1) | 70-80 |
| | IXP5 | SGGRGGRPL (SEQ ID NO: 14) | 10-20 |

$^a$Percentage of cells producing the indicated peptide from a SICLOPPS plasmid in conjunction with GFP-tag that have fluorescence intensity at least 0.5.times. that observed in ΔclpX cells producing GFP-tag, as determined by epifluorescence microscopy.

Cultures producing IXP1, IXP3, or IXP4 contained over 70% fluorescent cells, indicating efficient inhibition of GFP-tag degradation (Table 5). In addition, the ΔclpX strain has a partially penetrant filamentous phenotype, and cells producing IXP1, IXP3, or IXP4 had a similar morphology (FIG. 4C), suggesting that the presence of these peptides mimics a genetic deletion of clpX. Fewer than 40% of the cells producing IXP2 or IXP5 were fluorescent, suggesting low intracellular concentrations of the cyclic peptide or inefficient inhibition of GFP-tag degradation in these clones. Although there is some sequence similarity between pairs of inhibitory cyclic peptides, there is no sequence conservation in the randomized region found in all of the peptides, indicating that they may inhibit the degradation of GFP-tag through different interactions.

Inhibition of ClpXP in vitro: To ensure that the selected cyclic peptides are inhibitors of ClpXP and do not cause accumulation of GFP-tag in vivo by some other mechanism, cyclic peptides were synthesized and purified to examine their effects on ClpXP activity in vitro. Proteolysis of GFP-tag in the presence of ClpXP and SspB was monitored by loss of GFP fluorescence in a continuous fluorometric assay. In the absence of cyclic peptide, GFP-tag was degraded with kinetic parameters $k_{cat}$=1.79±0.08 min$^{-1}$, $K_m$=0.74±0.04 µM. No degradation was observed for GFP without a tmRNA tag or for GFP-tagDD when incubated with ClpXP and SspB. Likewise, no degradation was observed when ClpX or ClpP were omitted from the reaction. These results confirm that proteolysis of GFP-tag in vitro requires ClpXP recognition of the tmRNA peptide tag.

Figure 5:
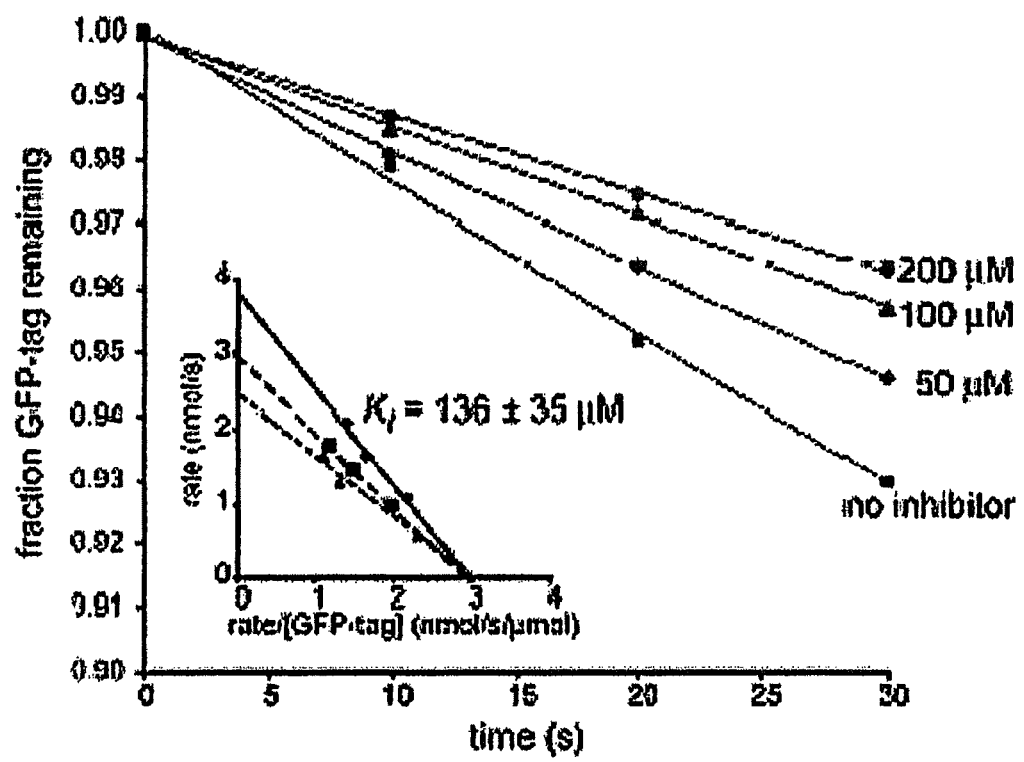
FIG. 5 is a graph showing cyclic IXP1 inhibits ClpXP in vitro. GFP-tag was incubated with ClpXP and proteolysis was monitored using a continuous fluorometric assay. Representative assays without inhibitor and with IXP1 are shown. The assays were repeated using different concentrations of substrate to determine the apparent kinetic parameters. Eadie-Hofstee plots (inset) for proteolysis with no inhibitor (solid line), 50 μM IXP1 (long dashes), and 100 μM IXP1 (short dashes), which are consistent with an uncompetitive inhibition model.

Inclusion of purified IXP1 reduced the rate of GFP-tag proteolysis, demonstrating that this cyclic peptide is a bona fide inhibitor of ClpXP (FIG. 5). Increasing the concentration of IXP1 decreased both the apparent KM and the apparent $k_{cat}$ of the reaction, suggesting uncompetitive inhibition. Fitting the data to an uncompetitive model gave a KI value of 136±35 µM (FIG. 5).

Figure 6A:
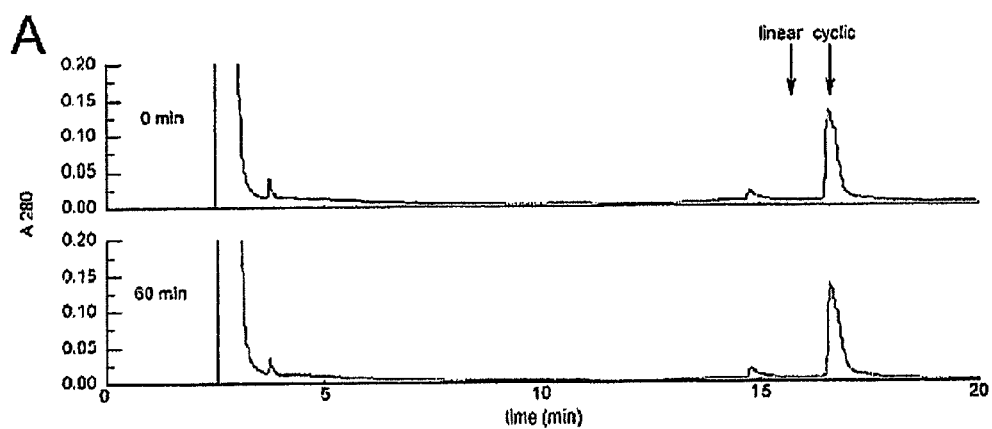
FIGS. 6A-6B show the interaction of IXP1 with ClpX and ClpP in vitro.
Figure 6B:
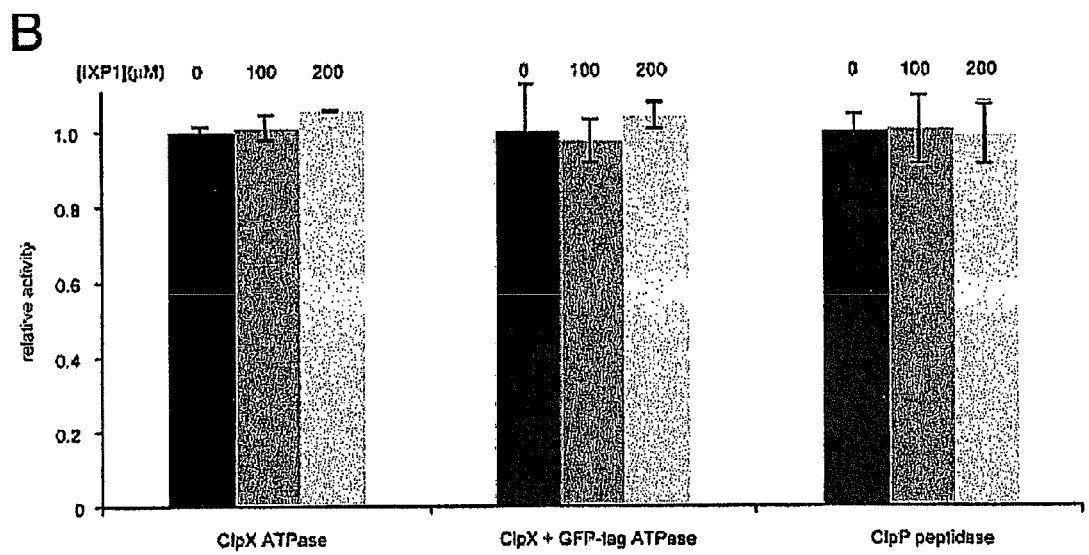

To exclude the possibility that IXP1 is a substrate for ClpXP, IXP1 was incubated with ClpXP in the absence of GFP-tag and the amount of cyclic peptide was quantified by reverse-phase HPLC. The amount of cyclic peptide did not change over at least one hour, and no linear peptide or smaller peptide products could be detected (FIGS. 6A-6B). These results indicate that IXP1 is not degraded by ClpXP.

The proteolytic mechanism of ClpXP involves both ATP-dependent unfolding of the substrate by ClpX and hydrolysis of peptide bonds by ClpP (Gottesman et al. 1997, Cell 91: 435-438), so the effects of IXP1 on these individual reactions were investigated. The rate of ClpX ATP hydrolysis was not inhibited by IXP1 at concentrations up to 200 µM (FIGS. 6A-6B). When GFP-tag was included in the ATPase assay the rate of hydrolysis increased by 1.6-fold, but IXP1 still had no effect on ClpX activity (FIGS. 6A-6B). The peptidase activity of ClpP was assayed using the fluorogenic substrate Suc-Leu-Tyr-AMC (Maurizi et al. 1994, Methods Enzymol 244: 314-331), and addition of IXP1 decreased ClpP activity by less than 2% (FIGS. 6A-6B). These results indicate that the individual activities of ClpXP are not affected by IXP1, and are consistent with an uncompetitive mechanism of inhibition.

Uncompetitive inhibition is characteristic of molecules that bind the enzyme-substrate complex, but not free enzyme. In the in vitro and in vivo proteolysis reactions above, the proteolytic adaptor SspB binds GFP-tag and tethers it to ClpXP (Levchenko et al. 2000, Science 289: 2354-2356). In principle, IXP1 could act on the GFP-tag.cndot.ClpXP interaction or the SspB.cndot.ClpXP interaction. Because ClpXP can degrade GFP-tag in the absence of SspB, albeit at a slower rate (Levchenko et al. 2000), the proteolysis assays were repeated without addition of SspB. The degradation of GFP-tag by ClpXP was still inhibited by IXP1 in the absence of SspB indicating that IXP1 binds the substrate-ClpXP complex.

Figure 7A:
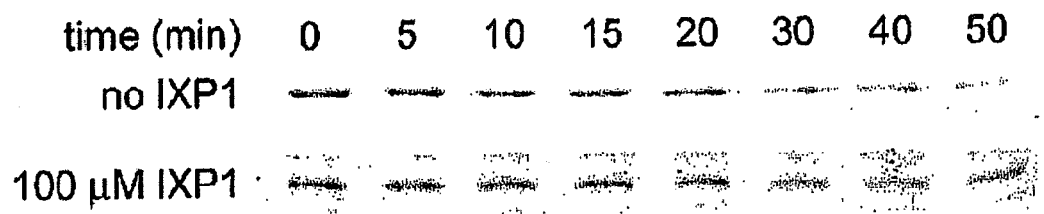
FIGS. 7A-7B show cyclic IXP1 inhibits degradation of λ O by ClpXP. λ O protein was incubated with ClpXP in the presence or absence of IXP1 and the loss of intact substrate was monitored by SDS-PAGE. Representative SDS-polyacrylamide gels stained with Coomassie blue showing the amount of λ O protein at various times after addition of ClpXP are shown (FIG. 7A). The amount of λ O protein remaining was plotted versus time and fit with a single exponential function to determine the substrate half-life (FIG. 7B). The average half-life for degradation of λ O was 35±2 min in the absence of IXP1, and 73±8 min in the presence of 100 μM IXP1.
Figure 7B:
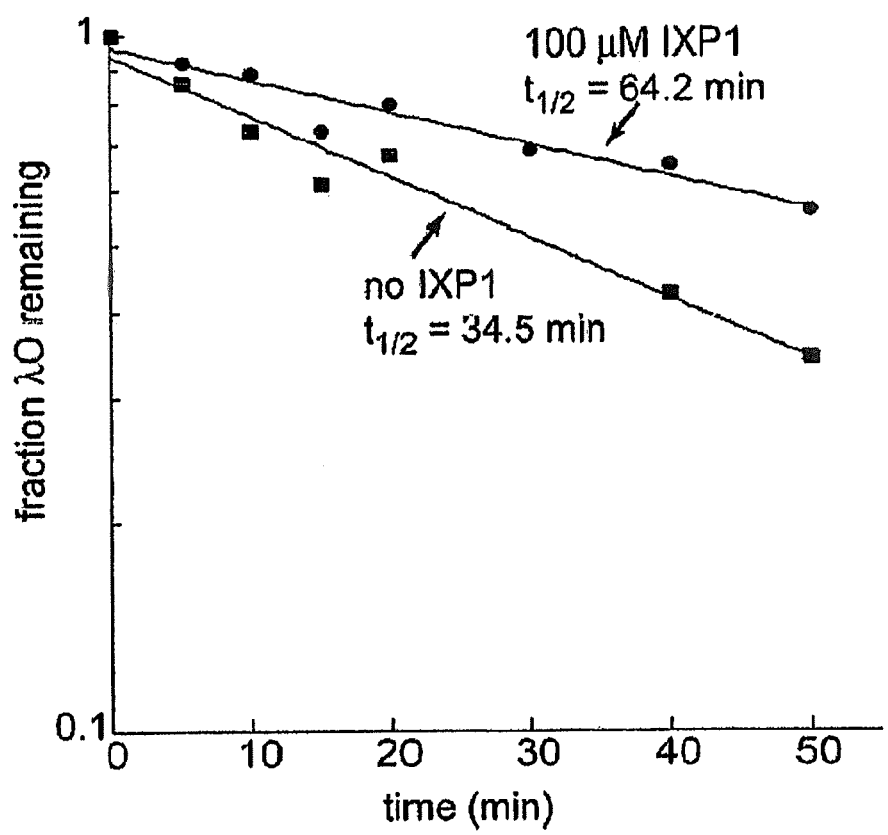
Figures 8A, 8B, 8C:
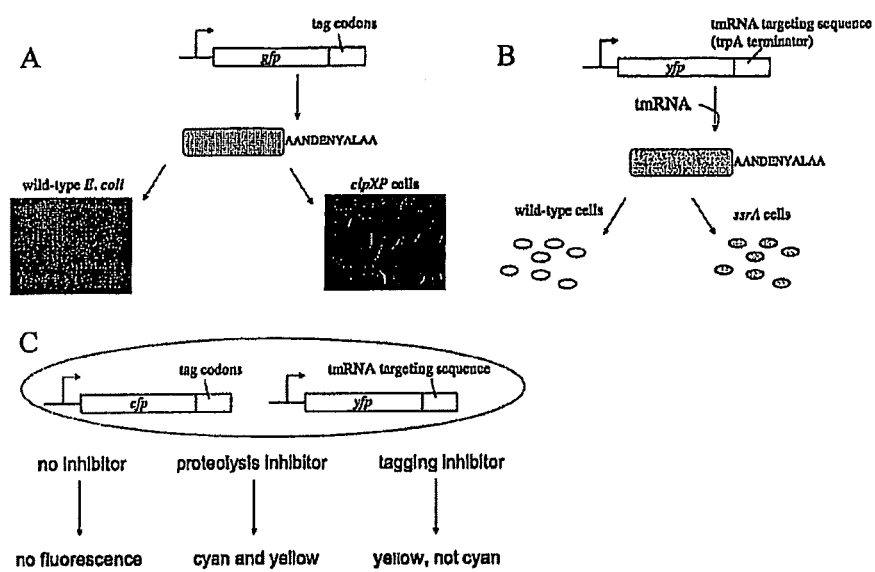
FIGS. 8A-8C constitute a schematic representation of tmRNA reporters.

Because ClpXP recognizes substrates by at least 5 different motifs, it has been proposed that there are several substrate binding sites on the protease (Flynn et al. 2003, Mol Cell 11: 671-683). To determine if IXP1 inhibits proteolysis of ClpXP substrates recognized by an epitope distinct from the tmRNA tag, λ O protein was used as an assay substrate. Sequences at the N terminus of λ O are recognized by ClpXP, and there is no interaction between λ O and SspB (Gonciarz-Swiatek et al. 1999, J Biol Chem 274: 13999-14005; Levchenko et al. 2000, Science 289: 2354-2356). Degradation of λ O was assayed in the presence and absence of IXP1 by following the loss of intact λ O protein on SDS-polyacrylamide gels (FIG. 7). With no inhibitor, λ O was degraded with a half-life of 35±12 min. Addition of 100 μM IXP1 increased the half-life to 73±18 min, close to the value expected if the $K_I$ with λ O was the same as for GFP-tag. Therefore, IXP1 is a general inhibitor of ClpXP and affects degradation of substrates in addition to those tagged by tmRNA.

Purified IXP3 and IXP4 also inhibited ClpXP in vitro, but appeared to be competitive inhibitors of GFP-tag degradation. IXP2 and IXP5 did not inhibit the reaction at the concentrations tested, consistent with the observation that fewer cells producing these peptides have high GFP-tag levels in vivo. The linear versions of IXP1, IXP2, IXP3, and IXP4 showed little inhibition of ClpXP in vitro at concentrations up to 1 mM, so the cyclic architecture of the peptides is important for inhibition (Table 6). An arbitrary cyclic peptide from the $SGWX_5$ library, Con62, also showed no detectable inhibition of ClpXP in vivo or in vitro at concentrations up to 1 mM (Tables 5 & 6). Therefore, both the sequence of the cyclic peptide and the cyclic architecture are important for inhibitory activity.

A linear peptide, XB, containing the 11 C-terminal residues of *E. coli* SspB, has been shown to bind to ClpX and inhibit the degradation of GFP-tag in the presence of SspB (Wah et al. 2003, Mol Cell 12: 355-363). IXP5 has some sequence similarity to the C terminus of SspB, indicating that cyclic versions of the XB peptide might also be potent inhibitors. To test this hypothesis, linear and cyclic versions of XB were synthesized and assayed in vitro (Table 6). The linear XB peptide was a competitive inhibitor of ClpXP degradation of GFP-tag in the presence of SspB, and the linear XB peptide had no effect on GFP-tag degradation in the absence of SspB and did not inhibit the degradation of λ O by ClpXP. Cyclic XB inhibited ClpXP proteolysis of GFP-tag in the presence of SspB with a $K_I$=8±1 μM, 7-fold lower than the linear XB peptide. Like linear XB, cyclic XB did not inhibit the degradation of λ O. Therefore, the circular ligation of the XB peptide increases the efficiency of inhibition, perhaps by decreasing the entropy of the free peptide, thereby increasing the energy of binding to ClpX.

Bactericidal activity of ClpXP inhibitors: ClpXP is important in *C. crescentus*, so the effect of adding purified inhibitory peptides to growing cultures was examined (Table 6). IXP1 killed *C. crescentus* with a minimum bactericidal concentration (MBC) of 279±23 μM and a minimum inhibitory concentration (MIC) of 219±42 μM, suggesting that IXP1 can both enter *C. crescentus* cells and inhibit *C. crescentus* ClpXP. The linear XB peptide had a MBC of 146±11 μM and a MIC of 139±44 μM, and the cyclic XB peptide was more effective, with a MBC 40±6 μM and a MIC 29±2 μM. Although *C. crescentus* has an SspB protein that performs the same functions as *E. coli* SspB, the sequence that interacts with ClpX is highly diverged (Lessner et al. 2007, J Bacteriol 189: 272-275). Nonetheless, all residues of *E. coli* ClpX that make hydrophobic or hydrogen-bonding contacts with the XB peptide (Park et al. 2007, J Mol Biol 367: 514-526) are conserved in *C. crescentus* ClpX, so the XB peptide might bind *C. crescentus* ClpX in the same manner as for *E. coli* ClpX. Cyclic peptides are not generally toxic to *C. crescentus*, because Con62 had no effect on bacterial growth. Thus, despite anticipated problems with transporting a peptide across the membrane of Gram-negative bacteria, peptides isolated from the screen had bactericidal activity.

TABLE 6

In vivo and in vitro properties of cyclic peptides.

| peptide | sequence | $K_I$ (μM)[a] | MIC (μM)[b] | MBC (μM)[b] |
|---|---|---|---|---|
| IXP1 | SGWYGRRH (SEQ ID NO: 6) | 13±6 ± 35 | 219 ± 42 | 279 ± 23 |
| linear IXP1 | SGWYGRRH (SEQ ID NO: 6) | >1000 | 385 ± 28 | 481 ± 38 |
| linear IXP2 | SGWHRRGM (SEQ ID NO: 5) | >400 | 304 ± 27 | 376 ± 37 |
| IXP2 | SGWRRGM (SEQ ID NO: 5) | >1000 | 430 ± 40 | >600 |
| Con62 | SGWPYKWM (SEQ ID NO: 4) | >1000 | >600 | >600 |
| Linear XB | CRGGRPALRVVK (SEQ ID NO: 3) | 56 ± 9 | 139 ± 44 | 146 ± 11 |
| cyclic XB | RGGRPALRVVK (SEQ ID NO: 15) | 8 ± 1 | 29 ± 2 | 40 ± 6 |

[a]Determined from kinetic assays with purified peptides and *E. coli* proteins.
[b]Values for addition of purified peptides to *C. crescentus* cells.

DISCUSSION: Using a high throughput screen and SICLOPPS technology, efficient inhibitors of the degradation of tmRNA-tagged proteins were isolated. Kinetic assays and several lines of evidence suggest that IXP1 is an uncompetitive inhibitor of ClpXP. IXP1 is not a substrate for ClpXP, but inhibits proteolysis of at least two ClpXP substrates that are recognized by different epitopes, and inhibition is independent of SspB, suggesting that IXP1 does not compete for binding to ClpX. IXP1 does not inhibit the ATPase activity of ClpX or the peptidase activity of ClpP, consistent with a mechanism in which IXP1 binds to the ClpXP-substrate complex. One step in the proteolytic mechanism where IXP1 could act uncompetitively is the translocation of the substrate through the central pore of ClpXP. Further structural and biochemical experiments will be required to understand exactly how IXP1 inhibits ClpXP, but it clearly does not use the same mechanism as the rationally designed peptide XB. Therefore, the screen described here can identify multiple inhibitors with diverse sequences and unexpected mechanisms of action. In principle, this screening technique could be employed to identify cyclic peptide inhibitors for any pathway with a fluorescent reporter that can be expressed in *E. coli*. The method provides a set of lead compounds for reagent design or antibiotic development that includes diverse activities, and does not require any knowledge of molecular structures or co-factor requirements of the targeted pathway.

The cyclic architecture of the selected peptides was important for the inhibitory and bactericidal activities. Because libraries of linear peptides have not been screened, it is possible that there are linear peptides that would inhibit ClpXP, but each of the selected cyclic peptide sequences was less effective in a linear form. Even the XB peptide, which inhibits ClpXP by binding to the same site as the C-terminal tail of SspB, is more active as a cyclic peptide. The higher activity of cyclic peptides compared to linear versions could be the result of specific structural features, or of tighter binding of cyclic peptides due to decreased loss of entropy. In either case, cyclic peptides are likely to be more stable in vivo than linear peptides, and are therefore more attractive for pharmacological and antibacterial agents. However, this does not rule out linear peptides. Although the selected cyclic peptides are bactericidal, optimization of the sequence and length of the cyclic peptides could improve their bioactivity. In principle, further improvements could be made through modification or derivatization of the peptide, or the use of non-standard amino acids. Finally, because the selected peptides appear to inhibit ClpXP through different interactions, using them in combination could have synergistic effects on the efficiency of inhibition. Even without improvements in efficiency, biologically active inhibitors such as IXP1 provide the ability to study the role of specific pathways in vivo without the drawbacks associated with the genetic deletion or depletion of essential activities.

Example 4

Reporter Construction

Development of reporters for the tmRNA pathway: To probe the activity of the tmRNA pathway, fluorescent reporters are developed for tmRNA activity and proteolysis of tagged proteins. A reporter for tmRNA activity is constructed by targeting the yellow fluorescent protein, EYFP, to the tmRNA pathway. This reporter probes all steps of the pathway and is used to identify inhibitors of tmRNA tagging and degradation of tagged proteins. An eyfp gene that produces mRNA with no stop codon is engineered by inserting a strong transcriptional terminator before the stop codon. Identical mutations in other genes have been shown to produce proteins tagged by tmRNA. This eyfp-trpAt gene is placed under the control of the IPTG-inducible promoter Ptrc, and integrated into a neutral locus of the E. coli K12 chromosome. When the tmRNA pathway is functional, the EYFP-trpAt protein should be tagged by tmRNA and degraded by proteases resulting in no accumulation of EYFP and no yellow fluorescence. However, if any step in the tmRNA pathway is blocked, the EYFP-trpAt protein should accumulate and produce yellow fluorescence within the cells. This behavior will be verified by ensuring that in wild-type E. coli K12 expressing EYFP-trpAt there is little fluorescence, but in an isogenic strain deleted for tmRNA there is significant yellow fluorescence. Inhibitors that block any essential step in the tmRNA pathway result in accumulation of EYFP from this reporter and produce yellow fluorescence in the cells. Although trpAt was used in the EYFP-trpAt construct described herein, any suitable tmRNA targeting sequence can be used in the compositions and methods described herein. Examples of additional tmRNA targeting sequences include: the protein sequences RLESG (weak stop) and P (weak stop) where "weak stop" is an inefficient translation terminator; sequences that result in mRNA cleavage, including more than two AGA codons or other rare codons, the sequences UAG, UCG or CAG that are cut by RelE, as well as other nuclease-recognition sites or self-cleaving RNAs; and sequences that terminate transcription before a stop codon is reached (e.g., any transcriptional terminator, but most commonly trpAt or rrnB cloned 5' of the stop codon in a gene). A tmRNA targeting sequence as described herein is any nucleic acid or protein sequence that results in tmRNA entering a translational complex (i.e., ribosome, mRNA, and nascent polypeptide).

A second reporter, specific for the proteolysis of tmRNA-tagged proteins has been generated. For this reporter, EGFP (enhanced green fluorescent protein) was targeted to ClpXP by adding codons for the 11 residue tmRNA peptide to the 3' end of the egfp gene. Although the protein (EGFP-tag) made from this gene is not targeted to the tmRNA pathway, it has the tmRNA peptide tag at the C terminus. A plasmid-borne version of this reporter (pEGFP-tag) was made by cloning egfp-tag under the control of the IPTG-inducible Ptrc promoter in a high copy number plasmid. Results demonstrate that the EGFP-tag protein made from pEGFP-tag is rapidly degraded in vivo and in vitro by ClpXP. Furthermore, wild-type E. coli bearing the pEGFP-tag reporter plasmid are not fluorescent even when expression of egfp-tag is induced by adding IPTG to the culture. Two controls indicate that proteolysis of EGFP-tag is through the normal tmRNA-ClpXP pathway. First, EGFP-tag is not degraded in a strain that is deleted for the clpX gene, and the cells are highly fluorescent when IPTG is added. Second, mutations known to disrupt the degradation of tmRNA-tagged proteins were made in the pEGFP-tag plasmid, and these mutations eliminate proteolysis of EGFP-tag. Changing the codons for the C-terminal amino acids in the tmRNA tag sequence from AA to DD is known to prevent degradation by ClpXP. When the terminal amino acids in pEGFP-tag were changed to DD, the resulting protein was stable and fluorescent in wild-type E. coli, and was not degraded by ClpXP in vitro. Therefore, the EGFP-tag reporter is degraded through the normal tmRNA-ClpXP pathway. As described below, pEGFP-tag has been successfully employed to select inhibitors of ClpXP. These experiments have demonstrated that the strategy for generating fluorescent reporters for the tmRNA pathway is effective.

It is possible that screening for tmRNA pathway inhibitors with the EYFP-trpAt reporter will preferentially yield inhibitors of tmRNA tagging, or of degradation of tagged proteins. If few inhibitors of degradation of tmRNA-tagged proteins are obtained from the EYFP-trpAt screen, a complete screen with EGFP-tag will be executed. To facilitate optimization and screening techniques, the EGFP-tag reporter is integrated into a neutral locus of the E. coli K12 chromosome. Conversely, if the EYFP-trpAt screen is dominated by ClpXP inhibitors, inhibitors of tmRNA tagging are selected using a strain with both the EYFP-trpAt and EGFP-tag reporters integrated into the chromosome. Because the fluorescence emission wavelengths for EGFP and EYFP are distinguishable, these reporters can be used in combination to identify inhibitors that target tmRNA but not ClpXP. A strain producing EGFP-tag and EYFP-trpAt will be fluorescent at green and yellow wavelengths in the presence of a ClpXP inhibitor because degradation of both reporter proteins will be blocked. In the presence of an inhibitor of tmRNA tagging, the EGFP-tag will be degraded but the tagging of EYPF-trpAt will be blocked, resulting in fluorescence at yellow wavelengths but not at green wavelengths. Cells with yellow fluorescence but no green fluorescence are selected by FACS as described below. Therefore, the EYFP-trpAt and EGFP-tag reporters enable selection of inhibitors of all reactions in the tmRNA pathway.

In certain embodiments the reporter is detectably labeled, and capable of generating a fluorescence energy signal. In the presence of an inhibitor, the activity will increase, and in the presence of an activator the activity will decrease. The reporter can be detectably labeled by covalently or non-covalently attaching a suitable molecule or moiety, for example any of various fluorescent materials (e.g., a fluorophore) selected according to the particular fluorescence energy technique to be employed, as known in the art and based upon the methods described herein. Fluorescent moieties and methods for as provided herein can be found, for example in Haugland (1996 Handbook of Fluorescent Probes and Research Chemicals-Sixth Ed., Molecular Probes, Eugene, Oreg.; 1999 Handbook of Fluorescent Probes and Research Chemicals-Seventh Ed., Molecular Probes, Eugene, Oreg., (probes.com/lit/) and in references cited therein. Particularly preferred for use as such a fluorophore in preferred embodiments are fluorescein, rhodamine, Texas Red, AlexaFluor-594, AlexaFluor-488, Oregon Green, BODIPY-FL, and Cy-5. However, any suitable fluorophore may be employed, and in certain embodiments fluorophores other than those listed may be preferred.

In another embodiment, the inhibition of tmRNA tagging is further identified using reporter strains expressing fluorescent labels. For example, the reaction that is targeted by each inhibitor is identified using EYFP-trpAt and EGFP-tag reporter strains Inhibitors of tmRNA tagging produce yellow fluorescence when incubated with the EYFP-trpAt strain, but no fluorescence when incubated with the EGFP-tag strain and inhibitors of proteolysis of tagged proteins produce fluorescence when incubated with either strain.

As provided herein, a fluorescence energy signal includes any fluorescence emission, excitation, energy transfer, quenching, or dequenching event or the like. Typically a fluorescence energy signal may be mediated by a fluorescent detectably labeled agent in response to light of an appropriate wavelength. Briefly, and without wishing to be bound by theory, generation of a fluorescence energy signal generally involves excitation of a fluorophore by an appropriate energy source (e.g., light of a suitable wavelength for the selected fluorescent moiety, or fluorophore) that transiently raises the energy state of the fluorophore from a ground state to an excited state. The excited fluorophore in turn emits energy in the form of detectable light typically having a different (e.g., usually longer) wavelength from that preferred for excitation, and in so doing returns to its energetic ground state. The methods of preferred embodiments contemplate the use of any fluorescence energy signal, depending on the particular fluorophore, substrate labeling method and detection instrumentation, which may be selected readily and without undue experimentation according to criteria with which those having ordinary skill in the art are familiar In certain embodiments, the fluorescence energy signal is a fluorescence polarization (FP) signal. In certain other embodiments, the fluorescence energy signal may be a fluorescence resonance energy transfer (FRET) signal. In certain other preferred embodiments the fluorescence energy signal can be a fluorescence quenching (FQ) signal or a fluorescence resonance spectroscopy (FRS) signal. (For details regarding FP, FRET, FQ and FRS, see, for example, WO97/39326; WO99/29894; Haugland, Handbook of Fluorescent Probes and Research Chemicals-6th Ed., 1996, Molecular Probes, Inc., Eugene, Oreg., p. 456; and references cited therein.)

FP, a measurement of the average angular displacement (due to molecular rotational diffusion) of a fluorophore that occurs between its absorption of a photon from an energy source and its subsequent emission of a photon, depends on the extent and rate of rotational diffusion during the excited state of the fluorophore, on molecular size and shape, on solution viscosity and on solution temperature (Perrin, 1926 J. Phys. Rad. 1:390). When viscosity and temperature are held constant, FP is directly related to the apparent molecular volume or size of the fluorophore. The polarization value is a ratio of fluorescence intensities measured in distinct planes (e.g., vertical and horizontal) and is therefore a dimensionless quantity that is unaffected by the intensity of the fluorophore.

The reporter can be labeled by covalently or non-covalently attaching a suitable molecule or moiety, for example any of various enzymes, fluorescent materials, luminescent materials, and radioactive materials. Examples of suitable enzymes include, but are not limited to, horseradish peroxidase, alkaline phosphatase, β-galactosidase, and acetylcholinesterase. Examples of suitable fluorescent materials include, but are not limited to, umbelliferone, fluorescein, fluorescein isothiocyanate, rhodamine, dichlorotriazinylamine fluorescein, dansyl chloride, phycoerythrin, Texas Red, AlexaFluor-594, AlexaFluor-488, Oregon Green, BODIPY-FL and Cy-5. Appropriate luminescent materials include, but are not limited to, luminol and suitable radioactive materials include radioactive phosphorus [$^{32}$P], iodine [$^{125}$I or $^{131}$I] or tritium [$^{3}$H].

In some embodiments, the fluorescence energy signal is a fluorescence polarization signal that can be detected using a spectrofluorimeter equipped with polarizing filters. For example, the fluorescence polarization assay is performed simultaneously in each of a plurality of reaction chambers that can be read using an LJL CRITERION™ Analyst (LJL Biosystems, Sunnyvale, Calif.) plate reader, for example, to provide a high throughput screen (HTS) having varied reaction components or conditions among the various reaction chambers. Examples of other suitable instruments for obtaining fluorescence polarization readings include the POLARSTAR™ (BMG Lab Technologies, Offenburg, Germany), BEACON™ (Panvera, Inc., Madison, Wis.) and the POLARION™ (Tecan, Inc., Research Triangle Park, N.C.) devices.

Some embodiments pertain in part to the use of intermolecular energy transfer to monitor tmRNA assays for the identification of inhibitors. Energy transfer (ET) is generated from a resonance interaction between two molecules: an energy-contributing "donor" molecule and an energy-receiving "acceptor" molecule. Energy transfer can occur when (1) the emission spectrum of the donor overlaps the absorption spectrum of the acceptor and (2) the donor and the acceptor are within a certain distance (for example, less than about 10 nm) of one another. The efficiency of energy transfer is dictated largely by the proximity of the donor and acceptor, and decreases as a power of 6 with distance. Measurements of ET thus strongly reflect the proximity of the acceptor and donor compounds, and changes in ET sensitively reflect changes in the proximity of the compounds such as, for example, association or dissociation of the donor and acceptor. In a preferred embodiment, one or more ET donor and an ET acceptor molecules are provided.

In certain preferred embodiments, a detectable signal that is generated by energy transfer between ET donor and acceptor molecules results from fluorescence resonance energy transfer (FRET). FRET occurs within a molecule, or between two different types of molecules, when energy from an excited donor fluorophore is transferred directly to an acceptor fluorophore (for a review, see Wu et al., Analytical Biochem. 218:1 13, 1994).

Identification of molecular targets: The reaction that is targeted by each inhibitor in vivo is identified using the EYFP-trpAt and EGFP-tag reporter strains. Inhibitors of tmRNA tagging should produce yellow fluorescence when incubated with the EYFP-trpAt strain, but no fluorescence when incubated with the EGFP-tag strain, whereas inhibitors of proteolysis of tagged proteins should produce fluorescence when incubated with either strain Inhibition of the relevant reaction is then confirmed using established in vitro assays with purified components. More specific assays are then used to determine which molecular interactions are inhibited by the cyclic peptide.

The tagging activity of tmRNA is assayed in a reconstituted in vitro translation system using poly(U) RNA as a template. This RNA has no stop codon, and is a substrate for tmRNA in vitro. Tagging is measured by incorporation of [$^{14}$C]-alanine into peptides, which can only occur through tmRNA tagging. An E. coli T7 coupled transcription/translation system (Promega) is used with the addition of tmRNA and poly(U). TCA is added to stop the reaction and precipitate peptides, which are collected on a glass fiber filter under vacuum. The incorporation of [$^{14}$C]-alanine is determined by scintillation counting. The inhibition of this reaction by purified cyclic peptides is determined by including increasing amounts of peptide in the reaction. A non-inhibiting peptide is used as a negative control. If tagging is inhibited, the steps that can be blocked are interaction of tmRNA with SmpB, and association of the tmRNA-SmpB complex with the ribosome. Because the E. coli reporter cells are viable during the screen, inhibitors of general translation factors such as alanyl-tRNA synthetase, EF-Tu, and the ribosome are not isolated. These factors are inhibited by existing classes of antibiotics and are not targeted in this project. The effect of peptides on the binding of SmpB to tmRNA is measured using filter-binding assays with purified SmpB and tmRNA generated from in vitro transcription. The $K_d$ for this interaction in the absence of inhibitor is 2 nM Inhibition of this interaction is assessed by incubating excess peptide and tmRNA with 0.5-50 nM SmpB and evaluating the percentage of SmpB that is bound to tmRNA. If inhibition is observed, the $K_I$ is determined to ensure that interaction with the peptide is specific and high affinity. If the peptide does not alter the interaction of SmpB and tmRNA, it is likely that inhibition occurs at the step of association of tmRNA entry into the ribosome.

Inhibition of ClpXP proteolysis is assayed in vitro using purified EGFP-tag as a substrate. Degradation of EGFP-tag by purified ClpXP is monitored by loss of fluorescence in a continuous spectroscopic assay (Levchenkco et al. (2000) Science 289, p. 2354). Inhibitors of ClpXP degradation could block binding of the tagged substrate by SspB, interaction of SspB with ClpX, assembly of the ClpXP multi-subunit complex, substrate binding by ClpX, or inhibit the proteolytic active site of ClpP. Spectroscopic proteolysis assays are performed using EGFP-tag, ClpXP, and purified cyclic peptide in the presence and absence of the proteolytic adaptor SspB. Assays are repeated with varying concentrations of peptide inhibitor to determine if the inhibition is competitive or non-competitive. Competitive inhibition of ClpXP in the absence of SspB indicates that the cyclic peptide is an active-site inhibitor of the protease. Non-competitive inhibition of proteolysis suggests that the cyclic peptide inactivates the protease by another mechanism, such as preventing association of the ClpX and ClpP subunits. In this case, the association of ClpX and ClpP can be assayed by gel filtration Inhibition of proteolysis only in the presence of SspB indicates that the cyclic peptide is interfering with the binding of SspB to the tagged protein, or with the binding of SspB to ClpX. Cross-linking and fluorescence anisotropy assays are available to test both of these interactions. These assays will elucidate the molecular target of cyclic peptide antibiotics, facilitating late-stage drug development.

Example 5

Luciferase-Based Reporter for tmRNA Activity

A reporter was constructed and tested using luciferase with one of three targeting sequences—a trpAt terminator, five threonine codons followed by a trpAt terminator, or five arginine codons followed by a trpAt terminator. This reporter has 20-fold higher activity in an E. coli strain that is deleted for tmRNA than in wild type, indicating that it could be used as a reporter for high-throughput screening for inhibitors of the tmRNA pathway. Other targeting sequences have been tested using fluorescent reporters (GFP, YFP, or mCherry), including a trpAt terminator, two sequential trpAt terminators, an rrnB terminator, a trpAt terminator followed by an rrnB terminator, five codons for threonine followed by trpAt, five codons for arginine followed by trpAt, two proline codons followed by an inefficient translational terminator followed by trpAt, codons for RLESG followed by an inefficient translational terminator followed by trpAt. Each of these constructs was expressed from three different promoters, Ptrc, Ptac, and T7. Because of the different background levels of expression, some reporters are optimized to identify inhibitors whereas others are optimized to identify activators.

The gene encoding firefly luciferase was amplified using PCR from plasmid pGL3 (Promega) and cloned into the vector pLC5 between an IPTG-inducible Ptrc promoter and a trpAt transcriptional terminator with no stop codon to generate the Ptrc-luc-trpAt reporter. The Ptrc-luc-(AGA)$_5$-trpAt and Ptrc-luc-(ACA)$_5$-trpAt constructs were made in a similar fashion, except that five AGA or ACA codons were inserted in the PCR primers. Any inducible or constitutive promoter sequence could be used in place of Ptrc, and any tmRNA-targeting sequence could be used in place of the trpAt, (AGA)$_5$-trpAt, or (ACA)$_5$-trpAt sequences, including any rho-dependent or intrinsic transcriptional termination sequence, any inefficient translational termination sequence, any ribonuclease cleavage site, or any ribosomal stalling sequence. E. coli cells bearing the reporter plasmids were grown to log-phase and production of the reporter protein was induced by the addition of IPTG. Cells were harvested and frozen before analysis of luciferase activity using the standard Luciferase Assay System or Dual-Luciferase Reporter Assay System (Promega) in a Bethold Lumat LB9501 for 10 s. For each sample, several dilutions were measured to ensure accuracy, and luminometer readings were normalized to the number of cells that were harvested.

Figure 9:
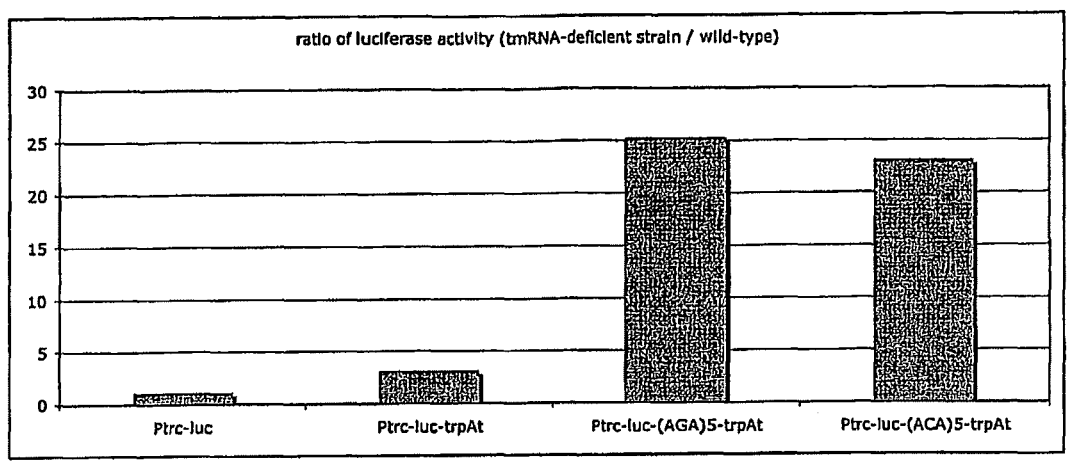
FIG. 9 is a graph showing the luciferase activity in a tmRNA deficient strain versus a wild type strain.

In the wild-type strain, the reporter is to be tagged and degraded by the tmRNA pathway, whereas in cells deleted for the gene encoding tmRNA the reporter should be stable and luminescence should be significantly higher. The Ptrc-luc-trpAt reporter showed 3-fold higher luciferase activity in the tmRNA-deficient strain than in wt, and the Ptrc-luc-(AGA)$_5$-trpAt and Ptrc(ACA)$_5$-trpAt reporters showed increases of 25-fold and 23-fold respectively. When no tmRNA targeting sequence was cloned downstream of the luciferase gene (Ptrc-luc), luciferase activity was identical in the two strains. (See FIG. 9).

Example 6

Additional Embodiments

As described above for the fluorescence-based constructs, in a luciferase reporter as described herein, any suitable tmRNA targeting sequence can be used. Examples of additional tmRNA targeting sequences include: the protein sequences RLESG (weak stop) and P (weak stop) where "weak stop" is an inefficient translation terminator; sequences that results in mRNA cleavage, including more than two AGA codons or other rare codons, the sequences UAG, UCG or CAG that are cut by RelE, as well as other nuclease-recognition sites or self-cleaving RNAs; and sequences that terminate transcription before a stop codon is reached (e.g., any transcriptional terminator, but most commonly trpAt or rrnB cloned 5' of the stop codon in a gene). In a typical embodiment, a luciferase-based construct for analyzing tmRNA activity in a cell includes two or more tmRNA targeting sequences. The two or more tmRNA targeting sequences can be identical, or they can be different from one another. In the luciferase-based experiments described above, the Ptrc-luc constructs contained trpAt in combination with either (ACA)5 or (AGA)5. However, any combination of tmRNA targeting sequences can be included in a reporter for analyzing tmRNA activity in a cell.

Compositions described herein also include luciferase-based reporters for analyzing proteolysis of tmRNA tagged proteins in a cell. Such a reporter is constructed using the reagents and methods described above for the construction of fluorescence-based reporters, except that the nucleic acid encoding a fluorescent protein (e.g., GFP) is replaced with a nucleic acid encoding luciferase.

A kit for screening for, identifying and/or characterizing an inhibitor (e.g., peptide, small molecule) of the tmRNA pathway is also described herein. In one example of a kit, the kit includes cells containing a reporter plasmid for analyzing tmRNA activity (e.g., plasmid encoding luciferase conjugated to a tmRNA targeting sequence), a reporter plasmid for analyzing proteolysis of tmRNA-tagged proteins (e.g., plasmid encoding luciferase conjugated to tmRNA peptide tag) in a single-tube or multi-well format (e.g., 96-well microtiter plate) for screening, and instructions for use. A kit will also generally further include appropriate controls. For example, three control strains can be included: a first strain with wild-type cells that would serve as a negative control, a second strain with cells deleted for tmRNA which would be positive for tagging and proteolysis, and a third strain with cells deleted for clpX which would be negative for tagging but positive for proteolysis. Individual plasmid DNA could also be included so that the user of the kit could make reporter strains in the desired genetic background.

Other Embodiments

It is to be understood that while the invention has been described in conjunction with the detailed description thereof, the foregoing description is intended to illustrate and not limit the scope of the invention. Other aspects, advantages, and modifications are within the scope of the following claims.

While the above specification contains many specifics, these should not be construed as limitations on the scope of the invention, but rather as examples of preferred embodiments thereof. Many other variations are possible.

All references cited herein, are incorporated herein by reference.

What is claimed is:

1. A non-natural nucleic acid construct comprising a nucleotide sequence encoding a promoter at a 5' end of the nucleic acid construct, operably linked to a nucleotide sequence encoding a luciferase variant sequence having no stop codon, which is operably linked to a nucleotide sequence encoding a tmRNA targeting sequence at a 3' end of the nucleic acid construct.

2. The nucleic acid construct of claim 1, wherein the nucleotide sequence encoding the tmRNA targeting sequence comprises at least two tmRNA targeting sequences.

3. The nucleic acid construct of claim 1, wherein the promoter comprises a constitutive promoter.

4. The nucleic acid construct of claim 1, wherein the promoter comprises an inducible promoter.

5. The nucleic acid construct of claim 2, wherein the at least two tmRNA targeting sequences comprise $(AGA)_5$ and a trpAt terminator sequence or $(ACA)_5$ and a trpAt terminator sequence.

6. The nucleic acid construct of claim 1, wherein the luciferase variant sequence comprises a firefly luciferase variant sequence.

7. A cell comprising a nucleic acid construct comprising a promoter at a 5' end of the nucleic acid construct, operably linked to a nucleotide sequence encoding a luciferase variant sequence having no stop codon, which is operably linked to at least one tmRNA targeting sequence at a 3' end of the nucleic acid construct, wherein the cell comprises a cell selected from the group consisting of a bacterial cell, a eukaryotic cell, and an archael cell.

8. The cell of claim 7, further comprising a cyclic-peptide expressing plasmid library which expresses cyclic peptides of at least about five amino acids to about twenty amino acids.

9. The cell of claim 8, wherein the cyclic peptide-expressing plasmid library is generated by randomly substituting at least 50% of nucleic acids coding for the cyclic peptides with an NNS sequence, wherein N=A, G, T, or C and S=G or C.

10. The cell of claim 8, wherein the cyclic peptide comprises one or more of SEQ ID NOs: 1-3, 5, 6, and 12-15.

11. The cell of claim 7, wherein the cell further comprises a second nucleic acid comprising a promoter operably linked to a nucleotide sequence encoding a luciferase variant sequence having no stop codon, which is operably linked at its 3' end to a nucleotide sequence encoding a tmRNA peptide tag.

12. The non-natural nucleic acid construct of claim 1, wherein the nucleotide sequence encoding a tmRNA targeting sequence comprises at least one codon sequence selected from the group consisting of AGA, ACA, UAG, UCG, and CAG.

* * * * *